US012773295B2

(12) United States Patent
Anderson et al.

(10) Patent No.: US 12,773,295 B2
(45) Date of Patent: Oct. 27, 2026

(54) IMMERSIVE THREE-DIMENSIONAL DISPLAY FOR ROBOTIC SURGERY

(71) Applicant: Verb Surgical Inc., Santa Clara, CA (US)

(72) Inventors: Kent Anderson, Mountain View, CA (US); Joan Savall, Palo Alto, CA (US); Brent Nobles, Palo Alto, CA (US); Allegra Shum, San Francisco, CA (US); Pablo E. Garcia Kilroy, Menlo Park, CA (US); Karen Shakespear Koenig, San Jose, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 19/094,737

(22) Filed: Mar. 28, 2025

(65) Prior Publication Data

US 2025/0221788 A1 Jul. 10, 2025

Related U.S. Application Data

(63) Continuation of application No. 18/488,022, filed on Oct. 16, 2023, now Pat. No. 12,290,413, which is a (Continued)

(51) Int. Cl.

*G06T 19/00* (2011.01)
*A61B 34/00* (2016.01)
(Continued)

(52) U.S. Cl.

CPC .............. *A61B 90/37* (2016.02); *A61B 34/25* (2016.02); *A61B 34/30* (2016.02); *A61B 34/35* (2016.02);
(Continued)

(58) Field of Classification Search

None
See application file for complete search history.

(56) References Cited

U.S. PATENT DOCUMENTS

| | | | | |
|---|---|---|---|---|
| 4,574,199 A * | 3/1986 | Pryor | .................. | G01B 11/007 33/503 |
| 5,243,665 A * | 9/1993 | Maney | ................ | H10P 72/0606 382/280 |

(Continued)

FOREIGN PATENT DOCUMENTS

| | | |
|---|---|---|
| CN | 102186434 A | 9/2011 |
| CN | 104918572 A | 9/2015 |

(Continued)

OTHER PUBLICATIONS

Advisory Action Office Action of the U.S. Patent Office dated Apr. 9, 2020 for related U.S. Appl. No. 15/724,185.

(Continued)

*Primary Examiner* — Frank F Huang
(74) *Attorney, Agent, or Firm* — Aikin & Gallant, LLP

(57) ABSTRACT

An immersive display for use in a robotic surgical system includes a support arm, a housing mounted to the support arm and configured to engage with a face of the user, at least two eyepiece assemblies disposed in the housing and configured to provide a three-dimensional display, and at least one sensor, wherein the sensor enables operation of the robotic surgical system, and wherein the support arm is actuatable to move the housing for ergonomic positioning.

20 Claims, 19 Drawing Sheets

Related U.S. Application Data continuation of application No. 17/819,843, filed on Aug. 15, 2022, now Pat. No. 11,813,122, which is a continuation of application No. 17/009,644, filed on Sep. 1, 2020, now Pat. No. 11,439,478, which is a continuation of application No. 15/724,185, filed on Oct. 3, 2017, now Pat. No. 10,786,327.

(60) Provisional application No. 62/403,655, filed on Oct. 3, 2016.

(51) Int. Cl.

| | |
|---|---|
| ***A61B 34/30*** | (2016.01) |
| ***A61B 34/35*** | (2016.01) |
| ***A61B 90/00*** | (2016.01) |
| ***A61B 90/50*** | (2016.01) |
| ***G06F 3/01*** | (2006.01) |
| ***H04N 13/344*** | (2018.01) |
| *A61B 17/00* | (2006.01) |

(52) U.S. Cl.

CPC .............. *A61B 34/74* (2016.02); *A61B 90/50* (2016.02); *G06F 3/012* (2013.01); *G06F 3/013* (2013.01); *G06T 19/006* (2013.01); *H04N 13/344* (2018.05); *A61B 2017/00199* (2013.01); *A61B 2017/00203* (2013.01); *A61B 2017/00207* (2013.01); *A61B 2017/00216* (2013.01); *A61B 2017/00973* (2013.01); *A61B 2090/365* (2016.02); *A61B 2090/372* (2016.02); *H04N 2213/001* (2013.01)

(56) References Cited

U.S. PATENT DOCUMENTS

| | | | | |
|---|---|---|---|---|
| 5,920,394 | A * | 7/1999 | Gelbart | G01S 17/66 356/615 |
| 8,535,336 | B2 * | 9/2013 | Trovato | A61B 17/3421 606/130 |
| 10,646,156 | B1 * | 5/2020 | Schnorr | G16H 50/20 |
| 10,883,708 | B2 * | 1/2021 | Chien | F21K 9/60 |
| 2003/0060927 | A1 | 3/2003 | Gerbi et al. | |
| 2003/0114962 | A1 | 6/2003 | Niemeyer | |
| 2005/0065658 | A1 | 3/2005 | Green | |
| 2007/0265495 | A1 | 11/2007 | Vayser | |
| 2008/0262312 | A1 * | 10/2008 | Carroll | A61B 1/00172 600/160 |
| 2009/0046146 | A1 * | 2/2009 | Hoyt | A61B 1/0004 345/169 |
| 2009/0088634 | A1 * | 4/2009 | Zhao | A61B 1/00193 600/425 |
| 2010/0079356 | A1 | 4/2010 | Hoellwarth | |
| 2010/0217991 | A1 | 8/2010 | Choi | |
| 2011/0118748 | A1 | 5/2011 | Itkowitz | |
| 2011/0118753 | A1 | 5/2011 | Itkowitz et al. | |
| 2014/0018960 | A1 | 1/2014 | Itkowitz | |
| 2014/0207541 | A1 * | 7/2014 | Nerayoff | G06Q 30/04 382/104 |
| 2014/0343404 | A1 | 11/2014 | Razzaque et al. | |
| 2015/0173846 | A1 * | 6/2015 | Schneider | G02B 27/017 600/424 |
| 2015/0230697 | A1 | 8/2015 | Phee et al. | |
| 2016/0000606 | A1 | 1/2016 | Spier | |
| 2016/0037998 | A1 | 2/2016 | Kawashima et al. | |
| 2016/0196694 | A1 | 7/2016 | Lindeman | |
| 2016/0220324 | A1 | 8/2016 | Tesar | |
| 2019/0223964 | A1 | 7/2019 | Navkar et al. | |
| 2019/0293935 | A1 * | 9/2019 | Schneider | A61B 90/37 |
| 2020/0138518 | A1 * | 5/2020 | Lang | A61B 34/10 |
| 2021/0192759 | A1 * | 6/2021 | Lang | A61B 90/37 |

FOREIGN PATENT DOCUMENTS

| | | | |
|---|---|---|---|
| CN | 105511632 | A | 4/2016 |
| JP | 08-196541 | A | 8/1996 |
| JP | 09-005633 | A | 1/1997 |
| JP | 10-254381 | A | 9/1998 |
| JP | 2003-225198 | A | 8/2003 |
| JP | 2003-250812 | A | 9/2003 |
| JP | 2004-305367 | A | 11/2004 |
| JP | 2013-510671 | A | 3/2013 |
| JP | 2014-094039 | A | 5/2014 |
| JP | 5737796 | B2 | 6/2015 |
| WO | 2010/021447 | A1 | 2/2010 |
| WO | 2012/075155 | A2 | 6/2012 |
| WO | 2014/155725 | A1 | 10/2014 |
| WO | 2016/133644 | A1 | 8/2016 |
| WO | 2018/057814 | A1 | 3/2018 |
| WO | 2018/067611 | A1 | 4/2018 |

OTHER PUBLICATIONS

Corrected Notice of Allowability of the U.S. Patent Office dated Aug. 26, 2020, for related U.S. Appl. No. 15/724,185.
Corrected Notice of Allowability of the U.S. Patent Office dated Jul. 8, 2020 for related U.S. Appl. No. 15/724,185.
Decision of Rejection of the Chinese Patent Office dated Oct. 14, 2020 for related Chinese Patent Application No. 201780003779.4.
Decision to Grant a Patent of the Japanese Patent Office dated Jul. 17, 2020 for related Japanese Patent Application No. 2019-512313.
Examination Report No. 1 of the Australian Patent Office dated Apr. 23, 2019 for related Australian Patent Application No. 2017339943.
Examination Report of the Australian Patent Office dated May 3, 2021 for related Australian Patent Application No. 2020200343.
Examiner's Report of the Canadian Patent Office dated Mar. 9, 2020 for related Canadian Patent Application No. 3,035,258.
Extended European Search Report of the EP Patent Office dated Apr. 23, 2020 for related EP Patent Application No. 17859051.9.
Final Office Action of the U.S. Patent Office dated Jan. 27, 2020 for related U.S. Appl. No. 15/724,185.
Final Office Action of the U.S. Patent Office dated Mar. 28, 2019 for related U.S. Appl. No. 15/724,185.
Grant of Patent of the Korean Patent Office dated Mar. 10, 2021 for related Korean Patent Application No. 10-2019-7006568.
International Preliminary Report on Patentability of the PCT dated Apr. 18, 2019 for related PCT Patent Application No PCT/US2017/054995.
International Preliminary Report on Patentability, mailed Apr. 18, 2019, for Application No. PCT/US2017/054995.
International Search Report and Written Opinion of the PCT dated Nov. 30, 2017 for related PCT Patent Application No. PCT/US2017/054995.
Non-Final Office Action of the U.S. Patent Office dated Aug. 28, 2019 for related U.S. Appl. No. 15/724,185.
Non-Final Office Action of the U.S. Patent Office dated Dec. 13, 2018 for related U.S. Appl. No. 15/724,185.
Non-Final Office Action received for U.S. Appl. No. 18/488,022, mailed on Sep. 9, 2024, 14 pages.
Notice of Acceptance of the Australian Patent Office dated Oct. 3, 2019 for related Australian Patent Application No. 2017339943.
Notice of Allowance of the U.S. Patent Office dated May 15, 2020 for related U.S. Appl. No. 15/724,185.
Notice of Allowance received for U.S. Appl. No. 18/488,022, mailed on Jan. 13, 2025, 5 pages.
Notice of Reasons for Refusal of the Japanese Patent Office dated Aug. 17, 2021 for related Japanese Patent Application No. 2020-141786.
Notification of Reasons for Refusal of the Japanese Patent Office dated Mar. 29, 2022 for related Japanese Patent Application No. 2020-141786.
Office Action of the Canadian Patent Office dated Dec. 15, 2020 for related Canadian Patent Application No. 3035258.
Office Action of the Chinese Patent Office dated Jul. 31, 2019 for related Chinese Patent Application No. 201780003779.4.

(56) References Cited

OTHER PUBLICATIONS

Office Action of the Chinese Patent Office dated Mar. 5, 2020 for related Chinese Patent Application No. 201780003779.4.
Office Action of the Japanese Patent Office dated Mar. 2, 2020 for related Japanese Patent Application No. 2019-512313.
Office Action of the Korean Patent Office dated Aug. 28, 2020 for related Korean Patent Application No. 10-2019-7006568.

* cited by examiner

IMMERSIVE THREE-DIMENSIONAL DISPLAY FOR ROBOTIC SURGERY

CROSS-REFERENCE TO RELATED APPLICATIONS

This application is a continuation application of U.S. patent application Ser. No. 18/488,022, filed on Oct. 16, 2023, which is continuation of U.S. patent application Ser. No. 17/819,843, filed on Aug. 15, 2022, now issued as U.S. Pat. No. 11,813,122 on Nov. 14, 2023, which is a continuation application of U.S. patent application Ser. No. 17/009,644, filed on Sep. 1, 2020, now issued as U.S. Pat. No. 11,439,478 on Sep. 13, 2022, which is a continuation application of U.S. patent application Ser. No. 15/724,185, filed on Oct. 3, 2017, now issued as U.S. Pat. No. 10,786,327 on Sep. 29, 2020, which claims priority to U.S. Patent Application No. 62/403,655, filed on Oct. 3, 2016, which are hereby incorporated by this reference in their entireties.

TECHNICAL FIELD

This disclosure relates generally to robotic or robotic-assisted systems and, more particularly, to immersive displays for use in robotic or robotic-assisted surgical systems.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. However, standard MIS systems have a number of drawbacks. For example, non-robotic MIS systems place higher demands on the surgeon, in part because they require surgeons to indirectly manipulate tissue via tools in a manner that may not be natural. Conventional robotic MIS systems, which may involve an operator viewing a display showing the endoscopic camera video feed and remotely operated to manipulate tools based on commands from an operator, may provide many benefits of MIS while reducing demands on the surgeon. However, such robotic MIS systems typically only have rigid, immovable displays that may lead to user strain, fatigue, and injury during use over long periods of time. Thus, it is desirable to have a display for use with robotic surgical systems.

SUMMARY

Generally, in one variation, an immersive display for use in a robotic surgical system comprises a support arm, a housing mounted to the support arm and configured to engage with a face of the user, at least two eyepiece assemblies disposed in the housing and configured to provide a three-dimensional display, and at least one sensor, wherein the sensor enables operation of the robotic surgical system; and wherein the support arm is actuatable to move the housing for ergonomic positioning. For example, the support arm may be articulated and comprise at least one or a plurality of actuatable joints.

The housing may include or be coupled to a contoured face frame that is configured to engage with the face of the user, and the face frame may include features such as padding for interfacing with the user, which may increase comfort and/or provide compliance for ergonomic positioning. Similar compliance with the respect to the face frame may be achieved in other manners, such as with a housing having multiple, movably compliant portions. For example, the support arm may be coupled to a first portion of the housing and the face frame may be coupled to a second portion of the housing that is movable (e.g., movably compliant) relative to the first portion of the housing.

The housing may include one or more of several additional features to improve the immersive display experience. For example, the immersive display may include one or more shields coupled to the housing, such as for blocking ambient light and peripheral visual distractions. At least one shield may be movable between a first position in which the shield is configured to obscure at least a portion of a field of view of the user, and a second position in which the shield is configured to reveal the portion of the field of view of the user. As another example, the immersive display may include at least one auxiliary display screen coupled to the housing, or any of various audio components such as a microphone and/or a speaker. A microphone may, for example, be coupled to the housing and configured to receive vocal commands for operation of the robotic surgical system. Furthermore, a speaker may be coupled to the housing and configured to provide audio information to the user. At least one haptic actuator may be coupled to the housing and configured to provide tactile feedback to the user. Furthermore, in some variations, the housing may include at least one tracking device coupled to the housing to monitor position of the housing.

The eyepiece assemblies may be configured to provide a three-dimensional display. For example, at least one of the eyepiece assemblies may be configured to display a left eye stereoscopic image and at least one of the eyepiece assemblies may be configured to display a right eye stereoscopic image, such that together the left eye and right eye stereoscopic images provide a three-dimensional display. For example, the three-dimensional display may be configured to display at least one image from an endoscopic camera used in the robotic surgical system. The eyepiece displays may additionally or alternatively be configured to display two-dimensional or other suitable content. In some variations, the immersive display may further include at least one auxiliary display coupled to the housing.

At least one sensor may be included as a safety feature of the robotic surgical system. For example, a sensor (e.g., in a camera or other suitable optical sensor configured to detect an iris code of a user) may be configured to identify the user for authorization to operate the robotic surgical system. As another example, a sensor (e.g., an optical sensor for performing eye-tracking) may be configured to determine proper alignment of eyes of the user with the eyepiece assemblies.

The immersive display may include other sensors for detecting head gestures of a user, performing eye-tracking, and/or detecting other user interactions, such that a controller may interpret the user interactions and have the immersive display respond appropriately. For example, in response to a detected head gesture of the user, the support arm may move the housing to track the head gesture (e.g., for ergonomic positioning). As another example, at least one sensor (e.g., pressure sensor, distance sensor, contact sensor, etc.) may be configured to monitor head gestures of the user for controlling operation of the robotic surgical system. As another example, at least one sensor may be an optical sensor configured to perform eye-tracking. As yet another example, the three-dimensional display may be configured to display a graphical user interface and at least one sensor may be configured to detect a head gesture for navigation of the graphical user interface.

As another example, the immersive display may be configured to display at least one image from an endoscopic camera used in the robotic surgical system. In response to at least one sensor detecting a head gesture, the three-dimensional display may be configured to display a modified image from an endoscopic camera. As an illustration, in response to the sensor detecting a forward-directed head gesture, the three-dimensional display may be configured to display a zoomed-in image from the endoscopic camera. As another illustration, in response to the sensor detecting a backward-directed head gesture, the three-dimensional display may be configured to display a zoomed-out image from the endoscope camera. Furthermore, in response to the sensor detecting a lateral head gesture, the three-dimensional display may be configured to display a panning image from the endoscopic camera, and in response to the sensor detecting a tilting head gesture, the three-dimensional display may be configured to display a tilting image from the endoscopic camera.

The immersive display may be configured to provide user positioning information. For example, the immersive display may provide guidance for maintaining a correspondence between a first relative spatial relationship of the eyepiece assemblies and user hand positions and a second relative spatial relationship of the endoscopic camera and a surgical instrument. For example, a three-dimensional display may be configured to display a visual cue for repositioning at least one of the housing and user hand positions.

As another example, the three-dimensional display may be configured to display a visual representation of a user hand position and/or a user foot position relative to at least one target position (e.g., location of a handheld user interface device, location of a foot pedal, etc.). The visual representation may be overlaid with a primary image, such as a camera view image.

In some variations, the immersive display may include at least one external camera coupled to the housing. The camera may, for example, be configured to provide at least one image of an environment external to the housing. For example, the three-dimensional display may be configured to selectively display the image of the environment external to the housing. Additionally or alternatively, the immersive display may include at least one external illuminator coupled to the housing, where the illuminator may be configured to project light onto an environment external to the housing.

DETAILED DESCRIPTION

Non-limiting examples of various aspects and variations of the invention are described herein and illustrated in the accompanying drawings.

Figure 1A:
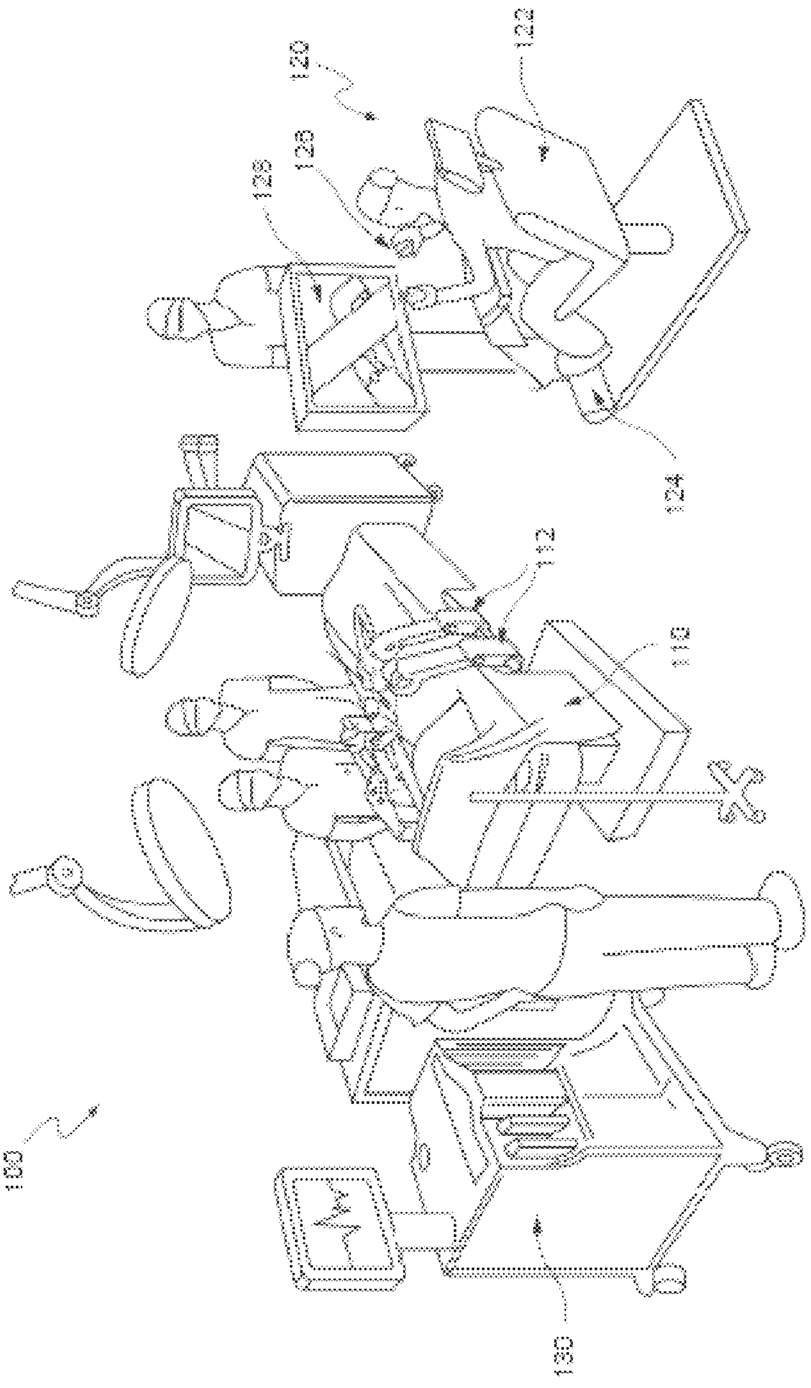
FIG. 1A is an overview schematic of an exemplary operating room arrangement with a robotic surgical system.

FIG. 1A is an illustration of an exemplary operating room environment with a robotic surgical system 100. As shown in FIG. 1A, the robotic surgical system 100 comprises a user console 120, a control tower 130, and one or more robotic arms 112 located at a robotic platform 110 (e.g., table, bed, etc.), where surgical instruments (e.g., with end effectors) are attached to the distal ends of the robotic arms 112 for executing a surgical procedure. The robotic arms 112 are shown as a table-mounted system, but in other configurations, the robotic arms may be mounted to a cart, ceiling or sidewall, or other suitable support surface.

Generally, a user, such as a surgeon or other operator, may use the user console 120 to remotely manipulate the robotic arms 112 and/or surgical instruments (e.g., in tele-operation). The user console 120 may be located in the same operating room as the robotic system 100, as shown in FIG. 1A. In other environments, the user console 120 may be located in an adjacent or nearby room, or tele-operated from a remote location in a different building, city, or country, etc. The user console 120 may comprise a seat 122, foot-operated controls 124, one or more handheld user interface devices 126, and at least one user display 128 configured to display, for example, a view of the surgical site inside a patient (e.g., captured with an endoscopic camera). As shown in the exemplary user console 120, a user located in the seat 122 and viewing the user display 128 may manipulate the foot-operated controls 124 and/or handheld user interface devices 126 to remotely control the robotic arms 112 and/or surgical instruments mounted to the distal ends of the arms.

In some variations, a user may operate the surgical robotic system 100 in an "over the bed" (OTB) mode, in which the user is at the patient's side and simultaneously manipulating a robotically-driven instrument/end effector attached thereto (e.g., with a handheld user interface device 126 held in one hand) and a manual laparoscopic tool. For example, the user's left hand may be manipulating a handheld user interface device 126 to control a robotic surgical component, while the user's right hand may be manipulating a manual laparoscopic tool. Accordingly, in these variations, the user may perform both robotic-assisted MIS and manual laparoscopic surgery on a patient.

During an exemplary procedure or surgery, the patient may be prepped and draped in a sterile fashion, and anesthesia may be achieved. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 120 may utilize the foot-operated controls 124, user interface devices 126, and/or other suitable controls to manipulate various end effectors and/or imaging systems to perform the surgery. Manual assistance may be provided at the procedure table by other personnel, who may perform tasks including but not limited to retracting tissues, or performing manual repositioning or tool exchange involving one or more robotic arms 112. Other personnel may be present to assist the user at the user console 120. When the procedure or surgery is completed, the robotic system 100 and/or user console 120 may be configured or set in a state to facilitate one or more post-operative procedures, including but not limited to robotic system 100 cleaning and/or sterilization, and/or healthcare record entry or printout, whether electronic or hard copy, such as via the user console 120.

In some variations, the communication between the robotic platform 110 and the user console 120 may be through the control tower 130, which may translate user commands from the user console 120 to robotic control commands and transmit them to the robotic platform 110. The control tower 130 may transmit status and feedback from the robotic platform 110 back to the user console 120. The connections between the robotic platform 110, the user console 120, and the control tower 130 may be via wired and/or wireless connections, and may be proprietary and/or performed using any of a variety of data communication protocols. Any wired connections may be built into the floor and/or walls or ceiling of the operating room. The robotic surgical system 100 may provide video output to one or more displays, including displays within the operating room as well as remote displays accessible via the Internet or other networks. The video output or feed may be encrypted to ensure privacy, and all or one or more portions of the video output may be saved to a server, an electronic healthcare record system, or other suitable storage medium.

Immersive Display System

Figure 1B:
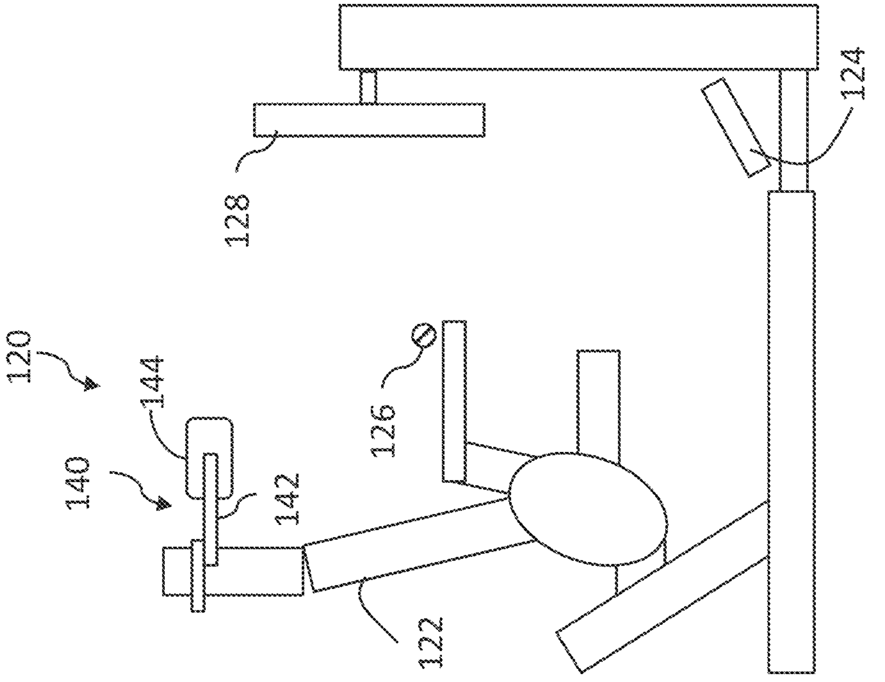
FIG. 1B is a side view of an exemplary user console with an exemplary immersive display, for use in a robotic surgical system.

As shown in FIG. 1B, an immersive display 140 may be part of a user console 120 for a robotic surgical system, along with an open display 128, a pedal assembly 124, and one or more handheld user interface devices 126. The immersive display 140 may display three-dimensional (3D) and/or two-dimensional (2D) information to a user in a manner that comfortably and ergonomically immerses the user into the display environment with reduced distractions from the user's peripheral field of view. The immersive display 140 (e.g., display housing 144 coupled to the seat 122 via a support arm 142) may display various information associated with the surgical procedure (e.g., endoscopic camera view of the surgical site, static images, GUIs, etc.) and/or robotic surgical system (e.g., status, system settings), and/or other suitable information in the form of 2D and 3D video, images, text, graphical interfaces, warnings, controls, indicator lights, etc. Unlike other immersive and virtual reality head-mounted devices, which rely entirely on motion of the head-mounted display to change the view of within the display and thus restrict the ability of head movements to control other instruments, the immersive display 140 as described herein may enable the user to interact with displayed content using head gestures and other head/eye movements for control of the immersive display and operation of other instruments such as those in the robotic surgical system.

Figure 2A:
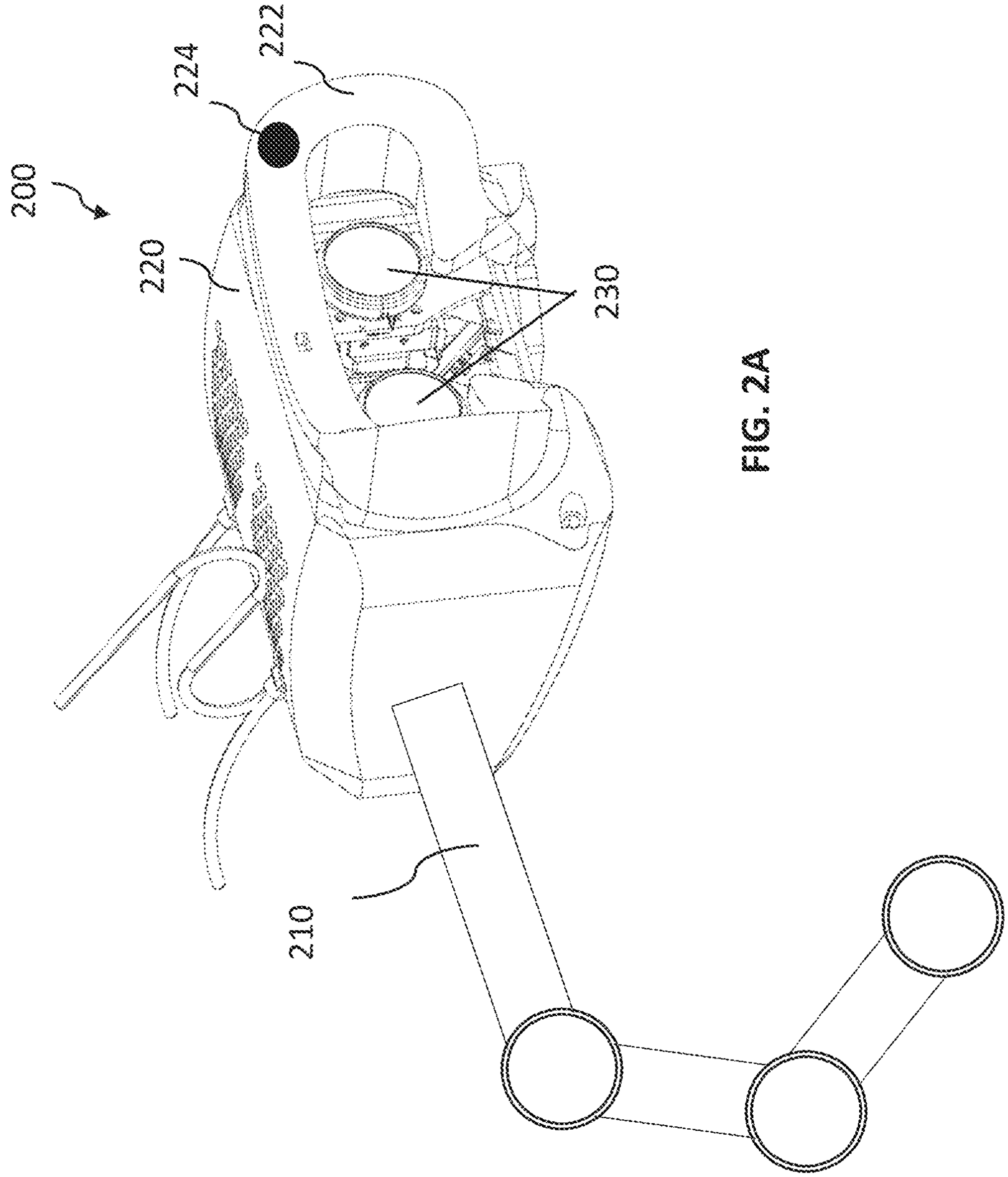
FIGS. 2A and 2B are perspective and partially exploded views, respectively, of one variation of an immersive display for use in a robotic surgical system.

Generally, as shown in FIG. 2A, an immersive display 200 may include a support arm 210 (partially shown in FIG. 2A), a housing 220 mounted to the support arm 210 and configured to engage with a face of a user, at least two eyepiece assemblies 230 disposed in the housing and configured to provide a three-dimensional display, and at least one sensor (e.g., represented by sensor 224 on a face frame 222 configured to engage the face of the user). The sensor may enable operation of the robotic surgical system upon detection of a certain parameter (e.g., presence or absence of a user engaged with the immersive display 200, sufficient alignment of the user relative to the eyepiece assemblies 220, identification of the user as an authorized user of the robotic surgical system, etc.), as described in further detail below. Additionally, the support arm 210 may be actuatable, such as for positioning, orienting, or otherwise moving the housing 220 for ergonomic purposes.

Support Arm

The support arm functions at least in part to support the weight of the housing, such that the user does not have to bear the weight of the housing (e.g., on the user's head or face) when the housing is engaged with the face of the user. As shown in FIG. 1B, a support arm 142 in the immersive display 140 may couple the immersive display housing 144 to a fixed structure such as a seat 122 or seat assembly. The support arm 142 may be configured to bring the housing 144 in position to engage the front of the user's face or head, although the immersive display may additionally or alternatively include straps or similar attachment devices to help secure the housing 144 to the user's face or head.

In some variations, the support arm 144 may be mounted on a seat back or headrest of the seat 122 and configured to approach the user from a side of the user console 120 to facilitate user access to the immersive display. For example, a proximal end of the immersive display support arm may be coupled to a right side of the seat back, though alternatively the proximal end of the display support arm may be coupled to a left side of the seat back (e.g., at about the height of the head rest, though not necessarily). The proximal end of the immersive display support arm may be configured to adjust vertically (e.g., with a prismatic joint) and/or rotationally, etc. Furthermore, the support arm may be configured to fold or collapse against the back or side of the seat (or other mounting location of the arm), so as to enable user access to the seat and/or facilitate storage or transport of the user console 120 in a compact configuration.

In other variations, a proximal end of the support arm 144 may be fixedly coupled to a midline (or near midline) of the seat back and configured to approach the user from the side of the user console 120 to facilitate user access to the immersive display. For example, a proximal end of the immersive display support arm may be fixedly mounted (e.g., via fasteners, welded joint, mechanical locks, etc.) to a posterior surface of the seat back of the seat 122. As another example, a proximal end of the immersive display support arm may be adjustably coupled to a posterior surface of the seat back, such as with a prismatic or other joint that enables the immersive display support arm to adjust vertically, laterally and/or rotationally relative to the seat back.

Figure 3A:
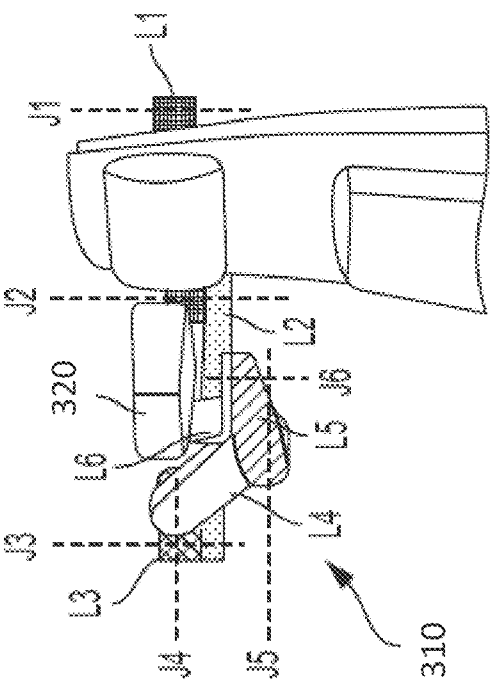
FIGS. 3A and 3B are detailed front and rear perspective views, respectively, of an exemplary support arm in one variation of an immersive display.

The immersive display support arm may be articulated such that it is capable of moving with multiple degrees of freedom, so as to position and orient the housing to a desirable state for the user. For example, in one exemplary variation shown in FIGS. 3A and 3B, an articulated immersive display support arm may include at least six degrees of freedom. In this paragraph, "horizontal" is meant in reference to being generally orthogonal to the seat back, while "vertical" is meant in reference to being generally parallel to the seat back. The support arm 310 may include a proximal mount coupled by a first rotational joint J1, such as a pin or fork joint, to a first link L1, where the first rotational joint J1 is rotatable around a vertical joint axis to provide movement in a horizontal plane. The first link L1 is coupled by a second rotational joint J2 to a second link L2, and second link L2 is coupled by a third rotational joint J3 to a third link J3. The first, second and third rotational joints J1, J2, and J3 are oriented along respective vertical rotation axes, and can permit adjustment of the immersive display without significant restriction at a desired location generally in a horizontal plane around the headrest region.

Further configurational flexibility is provided by the third link L3 being coupled by a fourth rotational joint J4 to a fourth link L4, where the fourth rotational joint J4 is rotatable around a horizontal axis to provide movement in a vertical plane. The fourth link L4 is further coupled by a fifth rotational joint J5 to a fifth link L5, where the fifth rotational joint J5 is rotatable around a horizontal axis to provide movement in a vertical plane. Furthermore, fifth link L5 is coupled by a sixth rotational joint J6 to a sixth link or bracket member L6, where the sixth rotational joint J6 is rotatable around a vertical axis to provide movement in a horizontal plane. The fourth, fifth, and sixth rotational joints J4, J5, and J7 generally permit vertical height adjustment of the immersive display such that in combination with the first, second, and third rotational joints J1, J2, and J3, all six rotational joints enable adjustments in various combinations of angular position changes in three-dimensional space (e.g., translation in X-Y-Z, rotation in yaw, roll, and pitch directions). The immersive display arm 310 may, as the result of multiple articulated joints having a suitable number of degrees of freedom may, for example, enable arm rotation, arm extension/retraction, arm forward/backward tilting, etc.

Figure 3B:
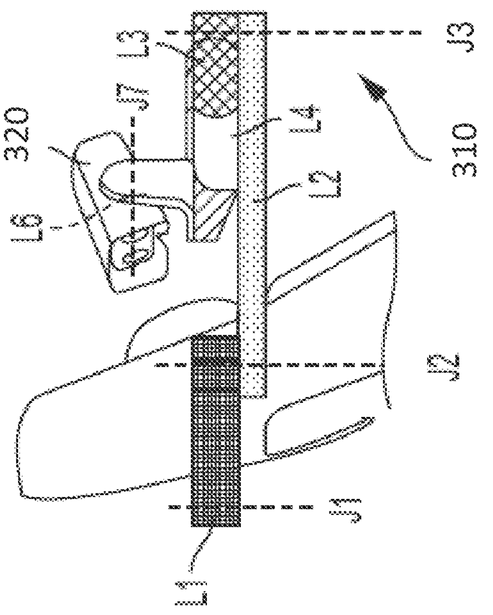

As shown in FIG. 3B, housing 320 may be mounted to bracket member L6 by a seventh rotational joint J7, where the seventh rotational joint J7 is rotatable around a horizontal axis so as to allow a seventh degree of freedom for pivotable adjustment in a vertical plane (e.g., angling up or down).

Some or all of the joints, such as the fourth and fifth joints J4 and J5, may include friction brakes, active brakes, clutch, and/or other actuatable locking mechanisms to help lock the immersive display support arm into a particular configuration. Locking the immersive display support arm in place may, for example, help counter gravitational effects that might cause the housing 320 and/or the support arm 310 to collapse downward (e.g., onto the user, if the seat assembly is in a reclined configuration). Additionally or alternatively, some or all of the joints may be counterbalanced in order to prevent downward collapse when unsupported externally by a user, etc.

Manipulations of the pose (i.e., location and/or orientation of parts of the arm) may be manually controlled and/or controlled with one or more actuators. Some movements of the arm may be automatic (e.g., collapse or extension) in response to a trigger, such as identification of a user present in the seat and ready to be engaged with the immersive display. Some movements of the arm may be triggered based on user input (e.g., as determined by sensors built into the support arm, handles coupled to the housing, etc.) and controlled by software. Manual adjustments of the arm may involve disengaging a clutch (e.g., with a touch sensor, button, handle, etc.) that is configured to resist movement of the arm.

In other variations, the support arm may include one substantially nonarticulated member. For example, the support arm may act as a static cantilever arm to suspend the immersive display generally in front of the seat assembly. In yet other variations, the support arm may include a member that swings laterally toward and away from a user in the seat assembly. For example, as shown in FIG. 4D, when the immersive display 400' is not in use, the support arm 410' may be oriented laterally outward in an "out" position to keep the housing 420' away from the face and head of the user. When the user is ready to engage the housing 420', as shown in FIG. 4E the display support arm 410' may then swing laterally inward in an "in" position to keep the housing 420' proximate to the face and head of the user.

Figure 3C:
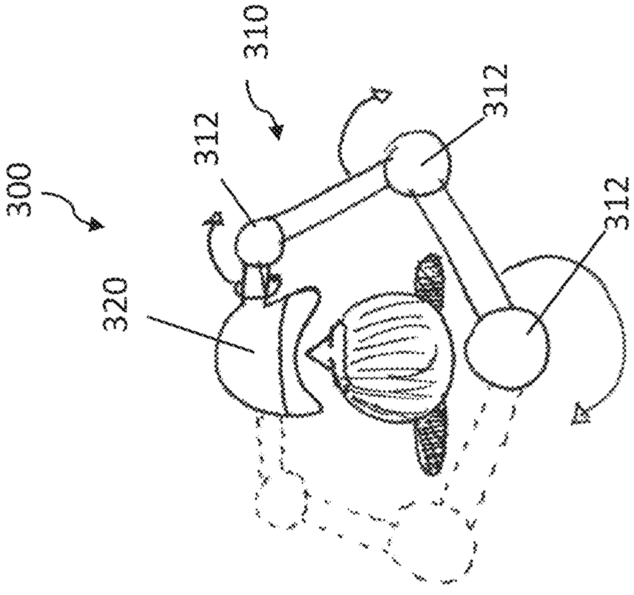
FIG. 3C is a top view schematic of an exemplary support arm that is configurable for a left-side or a right-side approach around the user, in one variation of an immersive display.

In variations in which a proximal end of the support arm is mounted to a side or to the midline (e.g., for vertical symmetry) of a seat back or other structure, the support arm may be configured to approach the user in the seat from either side. For example, in the schematic of an immersive display 300 shown in FIG. 3C, a proximal end of the support arm is mounted to a seat back or headrest located behind the user, and the support arm 310 wraps around a right side of the user and positions the housing 320 for engagement with the face of the user. However, a plurality of joints 312 in the support arm 310 may be configured to passively and/or actively rotate (clockwise direction as shown in FIG. 3C) to enable the support arm 310 to wrap around a left side of the user. Some or all joints (e.g., at least a proximal shoulder joint mounted to the seat back) may pivot such that at least some of the support arm is repositioned generally within a single plane, while at least some joints may be spherical joints or other suitable joints to permit any suitable ambidextrous reposing of the support arm 310 in space. For example, a distal yaw joint and/or tilt axis may enable the housing 320 to pivot in order to accommodate approach of the housing 320 from either side of the user.

Figure 4A:
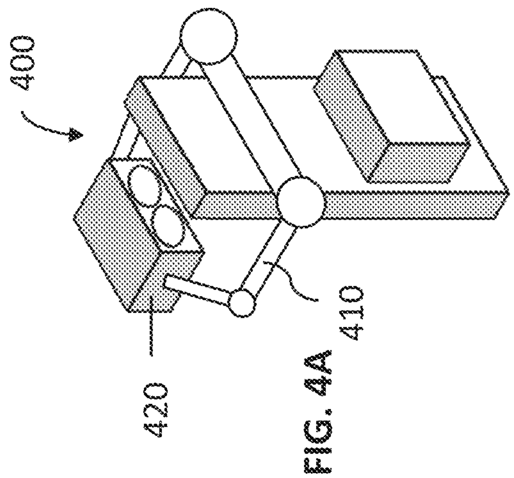
FIGS. 4A-4C are schematic illustrations of another exemplary overhead-style support arm frame in another variation of an immersive display.
Figure 4B:
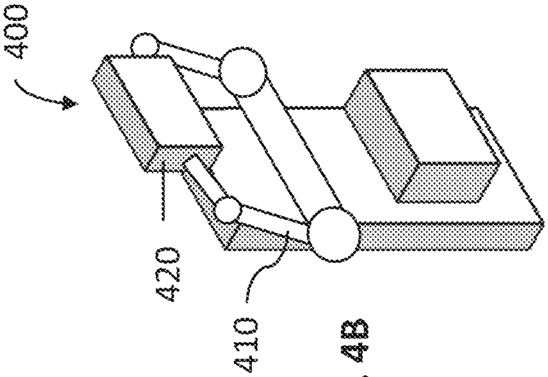
Figure 4C:
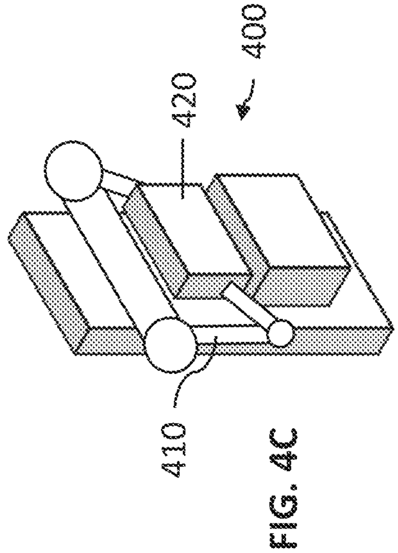
Figure 4E:
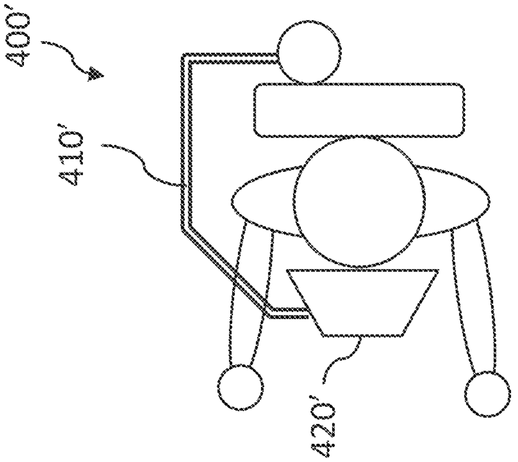
FIGS. 4D and 4E are schematic illustrations of another exemplary side-approach support arm in another variation of an immersive display.
Figure 4D:
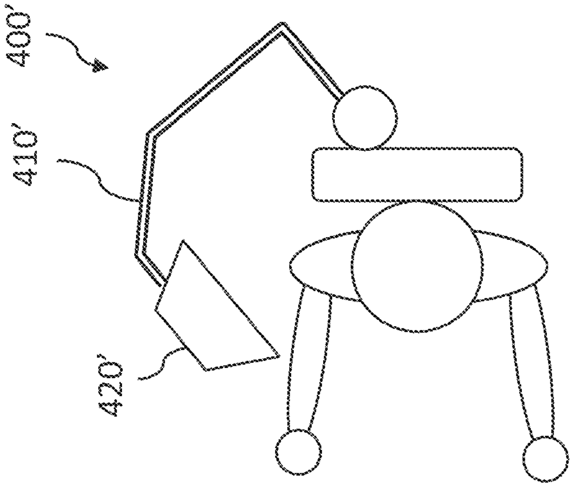

In yet other variations, as shown in FIGS. 4A-4C, the immersive display 400 may be coupled to the seat back (or headrest, etc.) with an overhead assembly including one or more support arms 410, such as in a support frame. The support arms 410 may be configured to approach the user from over the user's head as shown in FIG. 4A to allow the user to engage with housing 420. As shown in FIG. 4B, the support arms 410 may furthermore swing overhead to behind the headrest or other portion of the seat back, and the support arms 410 and/or housing 420 may fold down against the seat back (e.g., FIG. 4C) or collapse or recede into a cavity in the seat back, such as for storage purposes.

In some variations, the housing and/or support arm may include one or more sensors to aid in collision avoidance. For example, at least one proximity sensor (e.g., ultrasound, laser, etc.) may be located in at least a portion of the housing and/or support arm in order to detect potential collisions with the seat (e.g., seat back, armrest, headrest), open display monitor, the user's face or other body part, etc. Upon the detection of a potential collision, the immersive display may emit a warning, such as an audio tone, visual signal, tactile feedback through haptic motors, and/or the support arm may be actuated to remain in a "hold" position or move in an opposite direction so as to avoid collision between the support arm and another object.

Figure 5:
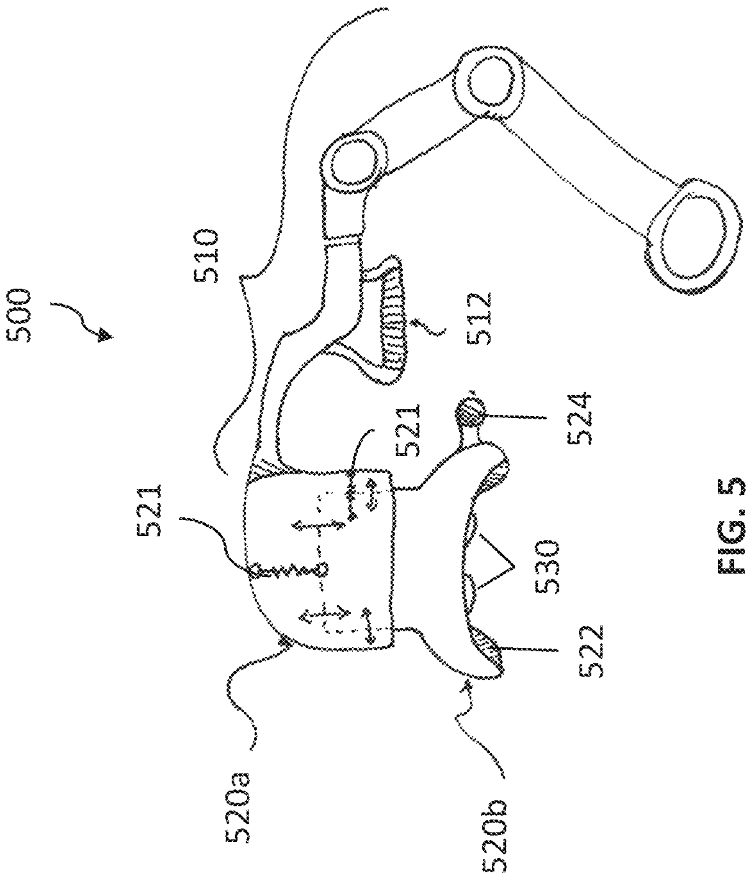
FIG. 5 is a top view schematic of an exemplary housing including movably compliant housing portions in another variation of an immersive display.

In some variations, the support arm may include structures to help a user manually move the arm. For example, as shown in FIG. 5, the support arm may include a handle 512 that may be grasped to reposition and repose the support arm as the result of pushing and/or pulling on the handle. Additionally, the handle may include sensors (e.g., pressure or contact sensors, capacitive sensors, etc.) to receive user input for further control of the immersive display, as further described below.

Figure 16A:
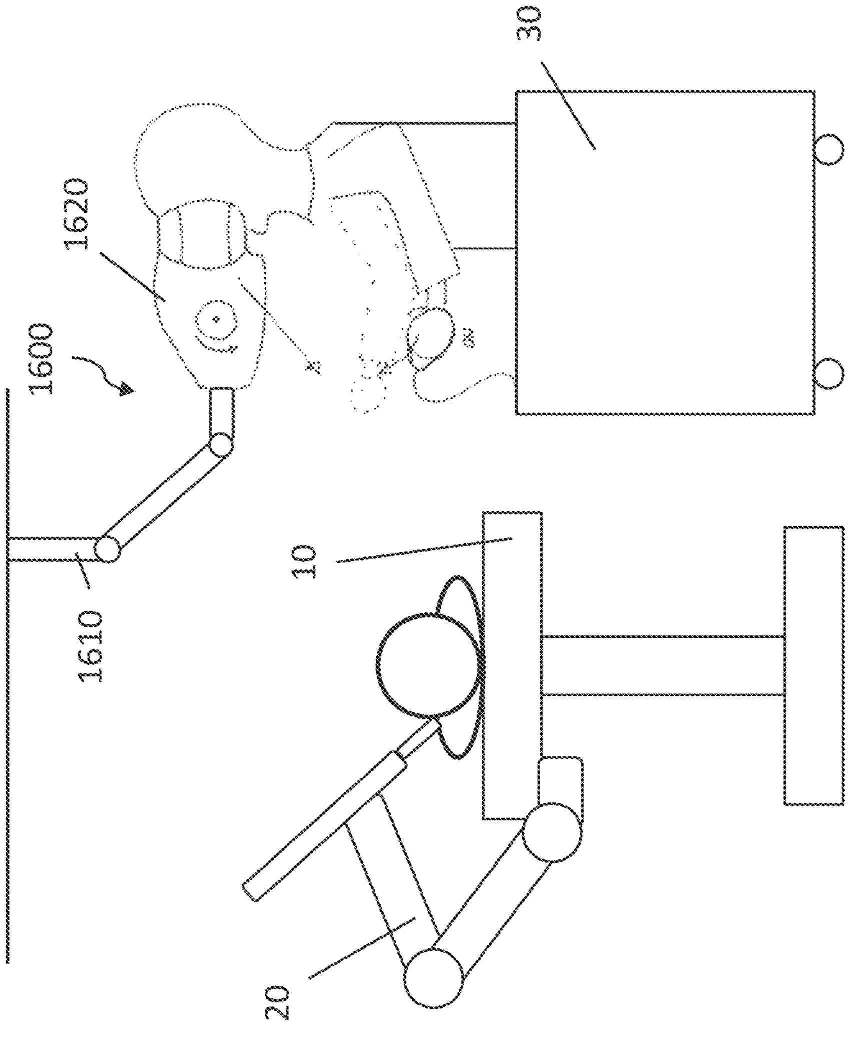
FIG. 16A is a schematic illustration of another variation of an immersive display, wherein the immersive display is mounted to a ceiling.
Figure 16B:
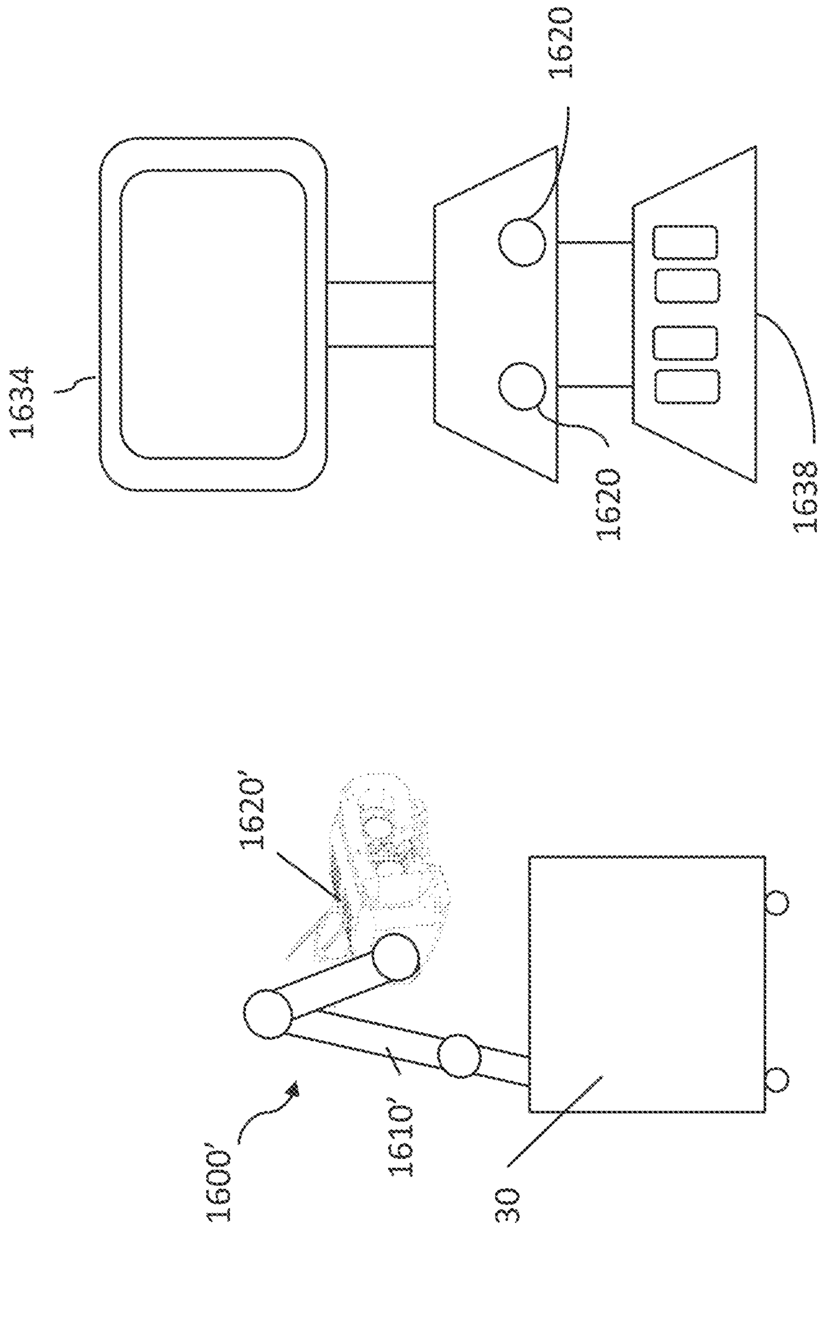
FIG. 16B is a schematic illustration of another variation of an immersive display, wherein the immersive display is mounted to a cart configured for use with a standing user console.

In other variations, the support arm may couple the housing to another suitable fixed structure, such as a ceiling or ceiling fixture, a column or wall, or a movable fixture such as a table or cart. For example, as shown in FIG. 16A, and immersive display 1600 may include a ceiling boom-type arm 1610 mounted to a ceiling or other upper fixture, and a housing 1620 coupled to the distal end of the arm 1610. In such a setup, the arm 1610 may be mounted overhead the patient on a table 10 or other surface with robotic arms 20, such that the user may be interfacing with the immersive display 1600 while standing (rather than sitting in a seat to which the immersive display is mounted) in a location where he or she may directly supervise the surgical procedure. In other variations, the arm 1610 may be mounted in any suitable location on the ceiling, wall, column, etc. A nearby cart 30 may provide additional components for controlling the robotic surgical system, such as handheld user interface devices. Alternatively, as shown in FIG. 16B, in another variation of immersive display 1600', the support arm 1610' may couple the display housing 1620' to a movable item such as a cart 30, which may permit transportation of the immersive display between different operating rooms. In some variations, the immersive display 1600' may be used in conjunction with a standing or desk-type user console such as that depicted in FIG. 16B, where a user may, while standing or sitting in a chair separate from the immersive display 1600', interact with an open display 1634, handheld user interface devices 1620, and foot-operated controls 1638, as well as selectively engage with the immersive display when desired. As another example, the support arm may be desk-mounted or mounted on another boom that is positionable for a user seated at an independent chair (e.g., stool or office chair), such as for use in an operating room or other room, and/or training purposes in an office setting. Furthermore, the support arm may be detachable from any of such fixed structures, so as to swap between different setups (e.g., transition between a chair-mounted immersive display, a ceiling-mounted immersive display, a wall-mounted immersive display, head-mounted display, etc.).

In yet other variations, it should be understood that the support arm may be omitted and the display housing may be mounted in any suitable manner, such as placed directly on a desk or other console system, or configured to be head-mounted (e.g., part of a helmet or including headstraps, etc.). For example, many of the concepts described herein (e.g., head gesture recognition, movable or pressure-sensing support cushions in the housing, eye-tracking, etc.) may be utilized in fixed binocular displays without a support arm structure.

Housing

Figure 2B:
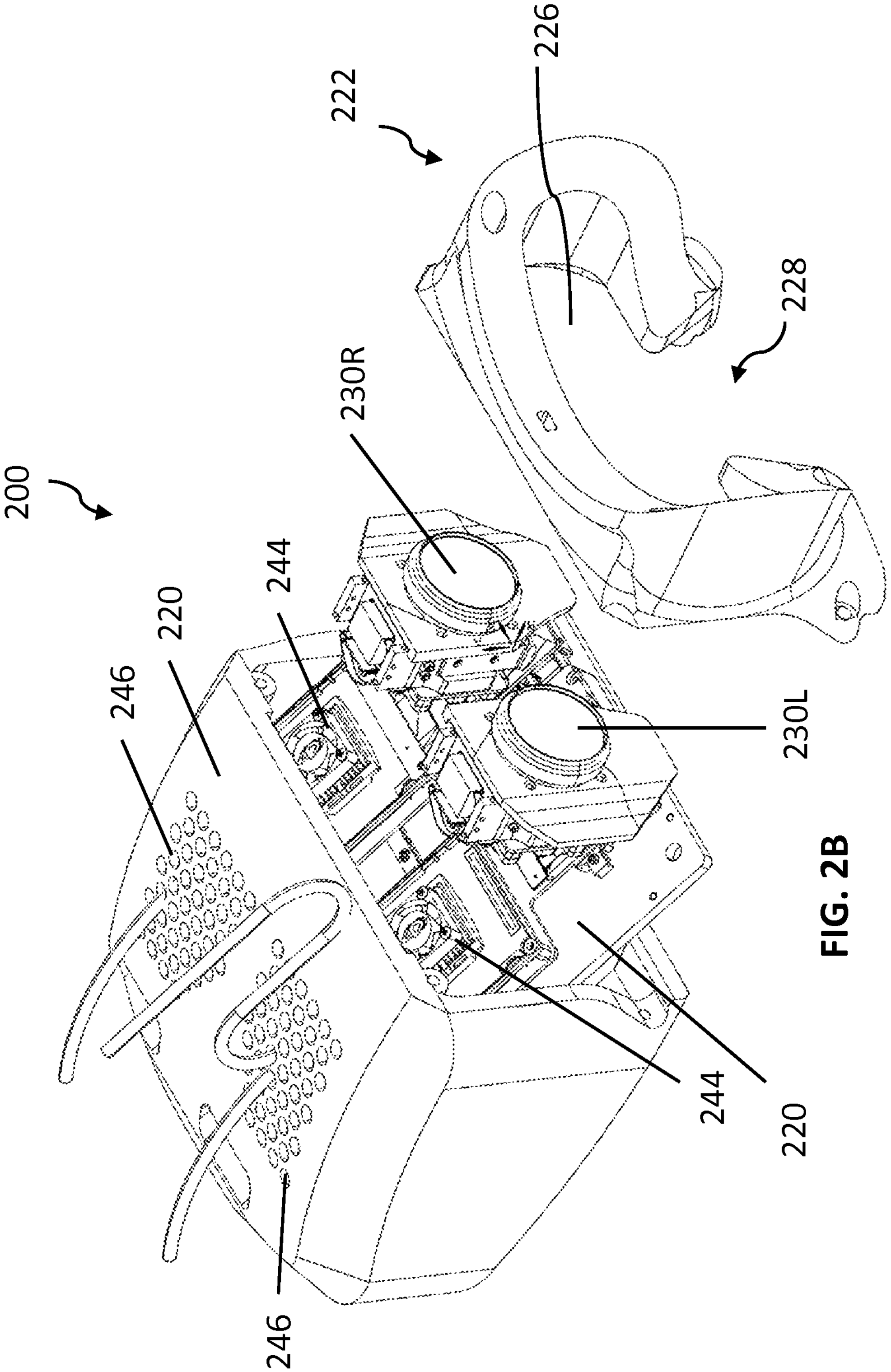

As shown in FIGS. 2A and 2B, the housing 220 provides an interface via face frame 222 for engaging with the face of a user, where the housing 220 at least partially encloses and protects the eyepieces assemblies and other display components. For example, as best shown in the partially exploded view of FIG. 2B, the housing 220 may be a receptacle including an internal volume that receives at least a left eyepiece assembly 230L and a right eyepiece assembly 230R. The housing 220 may be made of a relatively lightweight material (e.g., plastic) formed into a receptacle through any suitable combination of manufacturing methods (e.g., injection molding, machining, 3D printing, etc.). The housing 220 may be one integral piece, or may be a combination of assembled pieces, such as housing shells coupled together with fasteners, epoxy, etc. to form a receptacle.

In some variations, as best shown in FIG. 2B, the housing 220 may include openings or vents 246 to facilitate cooling of the internal volume of the housing 220. For example, there may be one or more fans 244 disposed within the housing, which are configured to direct flow of air in the housing toward vents 246 for exit out of the housing 220. In this manner, the fans and vents may generate negative pressure for pulling air away from the user's face and toward the vents 246, thereby keeping the user's face at a comfortable temperature, as well as helping to maintain suitable temperature environments for components within the housing.

As shown in FIGS. 2A and 2B, the housing 220 may include or be coupled to a face frame 222 or eye shroud. The face frame 222 may be configured to provide a comfortable, ergonomic interface between the housing 220 and the user's face. The face frame 222 may be contoured to receive a human face (e.g., generally concave), and include a window 226 (e.g., open or transparent to visible light) to leave the user's line of sight to the eyepiece assemblies unobstructed. The face frame 222 may include a cutout or other opening 228 to provide clearance for the user's nose and/or mouth. The face frame 222 may, in some variations, be configured to generally enshroud the eye region of the user.

Additionally, the face frame 222 may be configured to provide a reference guide for consistently positioning the user's face (and the user's eyes) at a correct or ideal distance from the eyepiece assembly optics for properly focused images, etc. For example, the dimensions of the face frame 222 may be selected so as to place the user's eyes a predetermined distance away from the eyepiece assemblies when the user's face is engaged with the face frame 222. The predetermined distance may be a coarse adjustment (e.g., while the eyepiece assembly positions may be slightly repositioned to provide a fine adjustment of depth), and/or be customized to the user to accommodate individual face shapes (e.g., large brow bones or cheekbones, relatively flat face, etc.).

In some variations, the face frame 222 may include a conformable or compliant material for increased comfort and/or ergonomics. For example, the face frame 222 may include padding such as cushioning, foam (e.g., shape memory foam), an inflatable structure, etc. on a patient-interfacing side of the face frame, and/or other compliant materials such as rubber gaskets or springs that couple the face frame 222 to the rest of the housing 220. Accordingly, the integral compliance in the face frame 222 (and/or between the face frame 22 and the housing 220) may allow the user to make minor positional adjustments without disengaging his or her face from the housing. For example, the user may slightly adjust his or her posture without interrupting workflow. Such minor adjustments may improve the immersive experience of the user in the 3D display and improve ergonomics.

Additionally or alternatively, the face frame 222 may include other mechanisms for conforming or adapting to the shape of a user's face. For example, a patient-interfacing side of the face frame 222 may include multiple elements (e.g., soft-tipped pins) that are individually movable axially in response to pressure from the surface of the user's face. As another example, a patient-interfacing side of the face frame 22 may include an accordion-like structure around the perimeter of the face frame that collapses in response to pressure from the surface of the user's face. An initial configuration of conformance to the user's face (e.g., during a setup phase of the immersive display) may provide a reference state, such that any changes in the conformance mechanisms relative to the reference state may be interpreted as user interactions (e.g., head gestures, as further described below). Conformance to the user's face may enable detection and recognition of relatively subtle facial expressions or other cues, which may be interpreted as user interactions for control of the system. Alternatively, in some variations, the distance between the face frame 222 and the user's face may incorporate a predetermined amount of clearance so as to accommodate a trackable workspace for head gestures detected by optical sensors, etc.

In one variation, as shown in FIG. 5, an immersive display 500 may include a first housing portion 520*a* and a second housing 520*b* that are movable relative to each other, such as through a sliding or nested engagement (e.g., with bearings). For example, the first housing portion 520*a* may include an outer shell configured to receive a portion of the second housing portion 520*b* with clearance, such that the second housing portion 520*b* may be free to move laterally side-to-side and/or forward and backward relative to the first housing portion 520*a*. Such relative movement may be compliant due to one or more springs 521 and/or other suitable compliant mechanisms. The support arm 520 may be attached to the first housing portion 520*a* (e.g., to a back portion or on the side of the first housing portion 520*a*), while the face frame 522 may be attached to the second housing portion 520*b*. In other variations, additional nesting or telescoping housing portions may be included in the immersive display. Accordingly, the integral compliance in the relative movement between the first and second housing portions may allow the user to make minor positional adjustments without disengaging his or her face from the housing. For example, the user may slightly adjust his or her posture without interrupting workflow. Such minor adjustments may improve the immersive experience of the user in the 3D display. Furthermore, since postural adjustments are key to reducing user and strain over extended, long-term use of the system, the multiple housing portions that are movably compliant relative to one another may help improve the ergonomic characteristics of the immersive display 500. Kinematics of the first and second housing portions (and/or of the support arm) may be configured such that a remote center of rotation of the immersive display generally coincides with a point estimated or predicted to be the user's neck. This might, for example, permit natural adjustments of the support arm and display for further improved ergonomic relief as the user moves his or her head.

In some variations, the face frame 222 may be removable from the housing 220, such as for sterilization (e.g., wipe-down with sterilization solution, sterilization in an autoclave, etc.) and/or enabling the exchange of different face frames 222 customized for different face shape types. The face frame 222 may, for example, be removably coupled to the housing with fasteners (e.g., screws, adhesive, etc.). Additionally or alternatively, the face frame 222 may be disposable, such as after a single use or limited number of uses.

One or more sensors (e.g., sensor 224) may be included on or near the face frame 222. For example, at least one sensor (e.g., pressure sensor, proximity or distance sensor such as an optical IR-based sensor, contact sensor temperature sensor, capacitive sensor, etc.) may be used to detect whether a user is engaged with the face frame 222. As described further below, the determination of the absence or presence of an engaged user may be used as part of a safety lock-out or interlock feature for restricting operation of the robotic surgical system. Furthermore, the detected absence of a user engaged with the immersive display may automatically result in another open display (e.g., display 128 as shown in FIG. 1A) serving as a primary display (e.g., with endoscopic camera view or other primary image content), while the immersive display optionally serves as a secondary display (with secondary image content). In contrast, the detected presence of a user engaged with the immersive display may automatically result in the immersive display serving as the primary display, while another open display optionally serves as a secondary or auxiliary display. Additionally or alternatively, at least one sensor on or near the face frame 222 may be used to detect any misalignment or non-optimum positioning of the user's engagement with the immersive display, and trigger a signaling to the user for self-correction of the misalignment, or trigger an automatic adjustment (e.g., by actuating the support arm until the misalignment is corrected). One or more proximity sensors may additionally or alternatively be used to provide a comfortable engagement with the user's face with the face frame 222, such as by triggering actuation of a dampened or slowed "soft landing" effect as the face frame 222 and the user's face approach each other for engagement.

As another example, one or more of the sensors may be used to detect user interactions (e.g., head gestures) which may be used to change controls in the system, modify the immersive display content, adjust housing or support arm configurations, etc. For example, such sensors may include pressure sensors, capacitive sensors, optical sensors, etc. where a change in signal may indicate motion of the user's head. For example, when the user moves his or her head to the right, this motion generally results in increased pressure on the right side of the face frame 222 and decreased pressure on the left side of the face frame 222. Sensors detecting these changes in pressure may be used to determine the head gesture toward the right. As another example, contact sensors may detect shear forces on the surface of one or more cushions or other surfaces that may be used to indicate a head turn gesture. Any number of suitable sensors may be used and placed at any suitable locations on, along, or in, the immersive display.

Figure 15B:
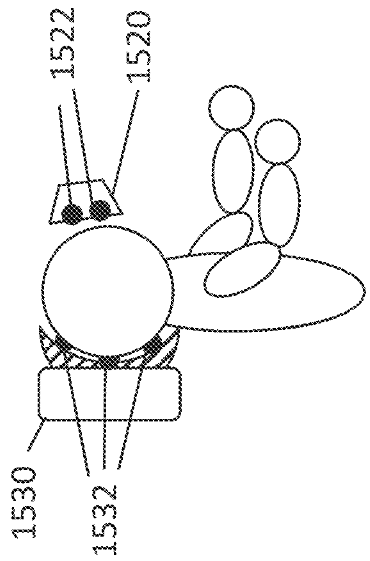
FIGS. 15A and 15B are top view and side view schematics of an exemplary immersive display setup with immersive display sensors working in cooperation with headrest sensors.
Figure 15A:
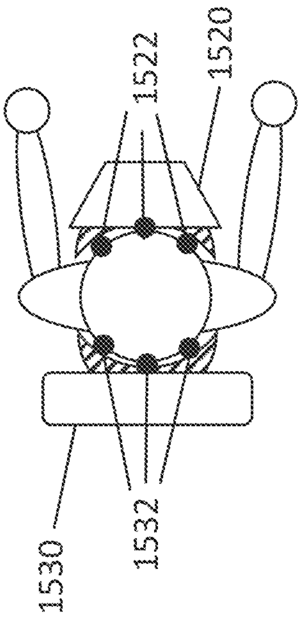

In some variations, as shown in FIGS. 15A and 15B, one or more sensors 1532 may alternatively or additionally (e.g., for redundancy) be included in a headrest 1530 behind the head of the user for detecting user interactions via head gestures. For example, a housing 1520 of the immersive display may include one or more sensors 1522 arranged generally on a left side, near the center, and/or on a right side of the housing 1520, and/or a headrest 1530 may include one or more sensors 1532 generally arranged on a left side, near the center, and/or on a right side of the headrest 1530, though other suitable arrangements of distributed sensors may be included in the immersive display and/or headrest. Information from these headrest sensors 1532 may be compared to or combined with information from the immersive display sensors 1522 to derive user intent. For example, head gestures and other head movements of the user may result in the back of the head providing inputs to the sensors 1532 in the headrest 1530 that are complementary to inputs to the sensors 1522 on the housing 1520 (e.g., when the user moves his her head to the right, this motion generally results in increased pressure on both the right side of the housing and the right side of the headrest), which may enable sensor redundancy. As another example, a combination of a lack of sensed pressure against the headrest and sensed pressure against the immersive display may indicate a first user intent (e.g., adjustment in posture), while a combination of sensed pressure against the headrest and sensed pressure against the immersive display may indicate a second user intent distinct from the first user intent.

As yet another example, one or more sensors on the face frame 222 (or elsewhere coupled to the housing or other components of the immersive display) may include one or more biometric sensors for monitoring parameters of the user. For example, the immersive display may include one or more EKG sensors for measuring heart activity, temperature sensors, heart rate sensors, blood pressure sensors, EEG sensors for measuring brain waves (e.g., to be placed on the user's temples), sweat sensors, other stress sensors, etc. Such biometric monitoring of the user while utilizing the immersive display may be useful for monitoring stress levels of the user, for gathering data for research or training purposes, etc. This biometric data may be stored in any suitable memory or storage device, such as a local storage device located in the immersive display (e.g., housing), other portion of the user console, other components of the robotic surgical system (e.g., a central unit on a cart, table, or control unit). Other examples of storage devices include portable flash memory (e.g., USB drives), remote computers or servers, cloud storage, etc.

Figure 6:
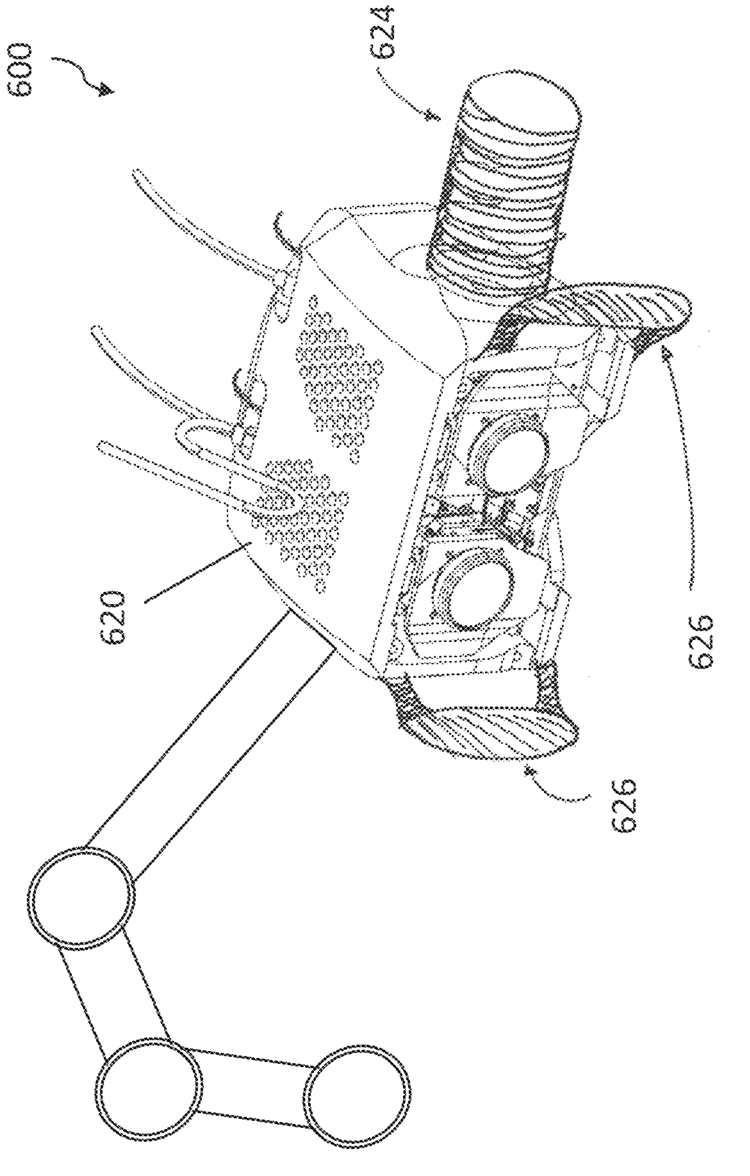
FIG. 6 is a perspective view of an exemplary housing including handles in another variation of an immersive display.

As shown in FIGS. 5 and 6, other variations of the housing may include one or more handles for manipulating (e.g., repositioning) the immersive display. For example, at least one handle 524 (FIG. 5) or 624 (FIG. 6) may be included on a side of the housing 520 or 620 (e.g., to facilitate a gross positioning mode in which large positional adjustments are performed, such as with enablement of a high number of degrees of freedom in the housing and/or support arm, with no or relatively few limitations on motions), and/or at least one handle 626 as shown in the immersive display 600 in FIG. 6 (e.g., to facilitate a fine positioning mode in which small or minor positional adjustments are performed, such as with enablement of fewer degrees of freedom in the housing and/or support arm, with more limitations on motions than in the gross positioning mode) on a side of the housing 620. Other suitable locations for handles also include a top or bottom exterior surface of the housing 620. In some variations, some handles may be located on both sides of the housing so as to permit ambidextrous use (e.g., a left side handle 626 and a right side handle 626). Some or all of the handles may include grips or bars as shown in FIG. 6, and/or a knob as shown in FIG. 5, though in other variations the handles may include rings, levers, and other suitable shapes for grasping. Additionally, at least some of the handles may include textural features to improve grip, such as finger grooves, ribbings, or bumps. As described in more detail below, at least some of the handles may include sensors (e.g., pressure, capacitive, etc.) for providing additional input for user interactions with the immersive display and/or for gathering biometric data (e.g., heart rate).

Figure 7:
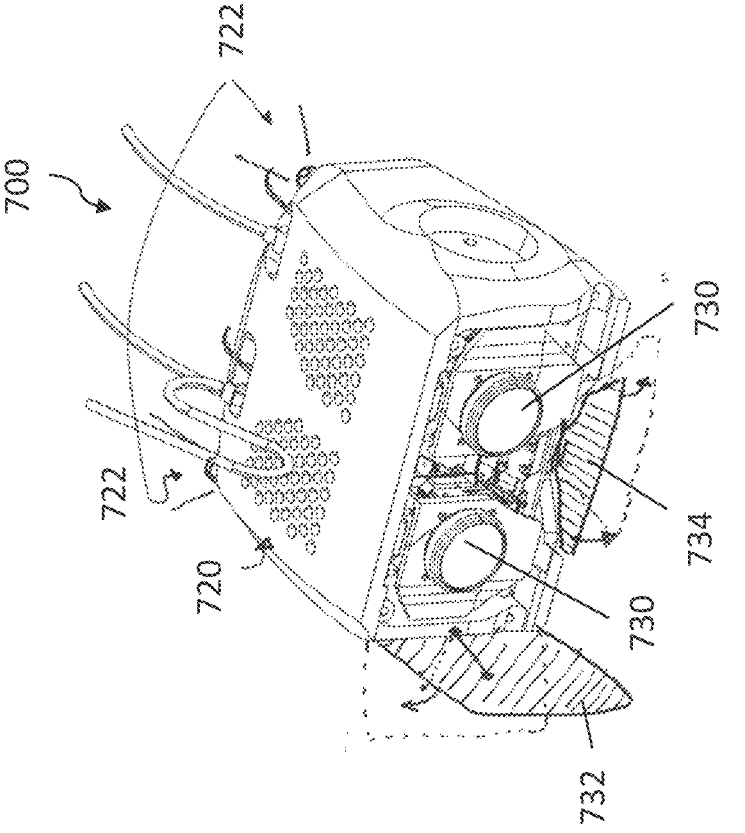
FIG. 7 is a perspective view of an exemplary housing including shields and outward-facing cameras in another variation of an immersive display.

As shown in FIG. 7, in some variations of an immersive display 700, the housing 720 may include at least one shield (e.g., side shield 732, lower shield 734) coupled to the housing configured to help block ambient light (from outside the housing) from entering the field of vision of the user, and/or help reduce visual distractions for the user, thereby improving the immersive experience when the user is viewing through the immersive display. However, in some instances, the user may wish to remove or reposition the shield to view and/or interact with the obstructed portions of his or her field of view. For example, the user may wish to view his or her hands (e.g., for locating or grasping handheld user interface devices) or feet (e.g., for locating pedals or other foot-operated controls) outside of the immersive environment. To accommodate such instances, the shield may be movable between a first position in which the shield is configured to obscure at least a portion of a field of view of the user, and a second position in which the shield is configured to reveal the portion of the field of view of the user. As such, the housing may be equipped with one or more suitable actuators for moving the shield between the first and second positions. The shield actuators may be triggered based on eye-tracking sensors, head gestures, input into user devices such as handheld user interface devices or foot-operated user interface devices, vocal commands, etc.

For example, as shown in FIG. 7, a housing 720 may include at least one side shield 732 disposed on the side of the housing. When the side shield 732 is engaged in the first position (indicated by the solid outline in FIG. 7), the side shield 732 may be configured to block a lateral peripheral portion of the user's field of view. The side shield 732 may be actuated to swing or pivot laterally outward into a second position (indicated by the dashed line in FIG. 7) to reveal the previously-obstructed lateral peripheral portion of the user's field of view. In other variations, instead of swinging laterally outward toward the second position, the side shield 732 may swing upward around an upper horizontal axis, or downward around a lower horizontal axis. In yet another variation, the side shield 732 may retract or collapse along the side of the housing (e.g., along a side wall of the housing 720, or within a slot in the side wall of the housing 720) to transition to the second position.

As another example, a housing 720 may include at least one lower shield 734 disposed on a lower portion of the housing. When the lower shield 734 is engaged in the first position (indicated by the solid outline in FIG. 7), the lower shield 734 may be configured to block a lower peripheral portion of the user's field of view. The lower shield 734 may be actuated to swing or pivot downward into a second position (indicated by the dashed line in FIG. 7) to reveal the previously-obstructed lower peripheral portion of the user's field of view. In other variations, the lower shield 734 may retract or collapse along the lower portion of the housing (e.g., along a lower wall of the housing 720, or within a slot along the lower wall of the housing 720) to transition to the second position. Similarly, the housing for the immersive display may include shields disposed in and/or around any suitable portions of the housing. Although the shields depicted in FIG. 7 are generally flap-like, other types of shields are possible, such as accordion-like, collapsible fabric shrouds.

Actuation of the one or more shields may occur as the result of user interactions. For example, sensors performing eye tracking may detect user glances (e.g., for at least a predetermined period of time, and/or in a particular direction toward a shield) and thereafter trigger actuation of one or more of the shields towards the second position to reveal the previously-obstructed view. For example, one or more sensors may detect when the user glances down toward a region blocked by the lower shield 734, and trigger the actuation of the lower shield 734 toward the second position. As another example, a pressure or force sensor on a side of the face frame may detect when the user presses his or her head against the side of the face frame toward the side shield 732, and trigger the actuation of the side shield 732 toward the second position. Accordingly, various sensors may enable the user to view his or her real environment outside the immersive environment, without requiring disengagement from the immersive display. Additionally or alternatively, the one or more shields may be manually moved between the first and second positions. Furthermore, the one or more shields may be biased toward either the first position or the second position (e.g., unless a bias force is overcome by a manual or actuated force, the shield may block a portion of the user's field of view), such as with a spring or other suitable bias mechanism (not shown).

As shown in FIG. 7, one variation of the housing 720 may include one or more cameras, such as outward-facing cameras 722 located on a side of the housing opposite the eyepiece assemblies 730. Outward-facing cameras may image the surrounding real environment and provide those images or video feed for display to the user on the immersive display such that the user may, if desired, view at least a portion of the surrounding real environment (e.g., in a "virtual window" mode that mimics viewing through a transparent or see-through housing) without disengaging from the immersive display. The outward-facing cameras 722 may be configured to provide different video feeds depending on their location. For example, as shown in FIG. 7, the outward-facing cameras 722 are located on a front surface of the housing 720 and are therefore configured to provide the user with contextual awareness of the real environment directly in front of the front surface of the housing 720. As another example, one or more outward-facing cameras may be located on a side of the housing 720 so as to provide the user with contextual awareness of the real environment directly next to the side of the housing 720. Such peripheral images may help provide the user with an expandable field of view of his or her real environment. In some variations, the user may selectively toggle between a display of a see-through view provided by the outward-facing cameras 722 and other displays of the immersive environment (e.g., endoscopic camera view) with user interactions detected by sensors. For example, if a user wishes to visually locate foot-operated controls positioned near his or her feet, the user may select the "virtual window" mode and tilt his or her face downwards (while engaged with the housing 720) toward the foot-operated controls to "see" the foot-operated controls via the video feed provided by the forward-facing cameras 722.

Figure 8:
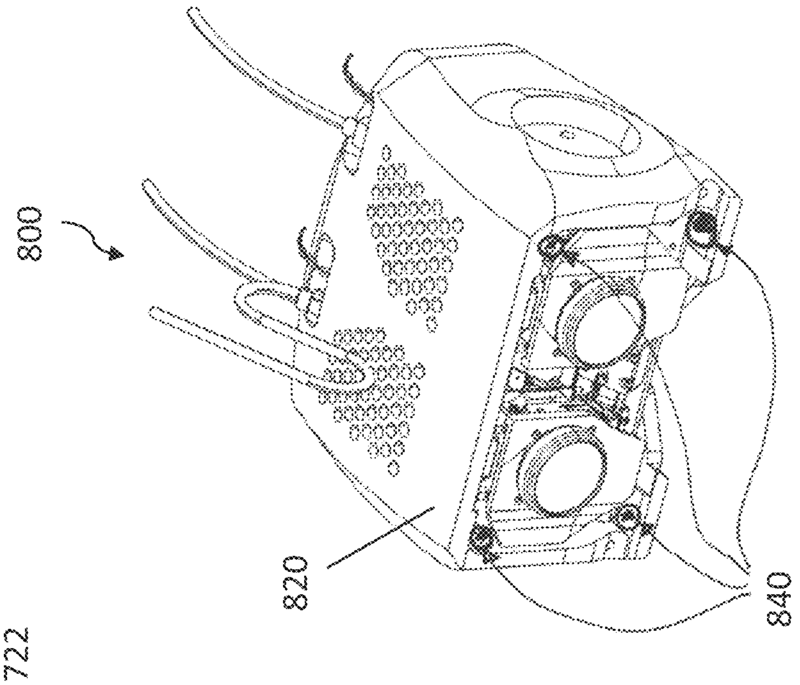
FIG. 8 is a perspective view of an exemplary housing including haptic actuators in another variation of an immersive display.

As shown in FIG. 8, in some variations, in an immersive display 800, a housing 820 may include one or more haptic actuators 840 configured to provide tactile feedback to the user. For example, the haptic actuators may include at least one vibration device (e.g., vibration motor, piezoelectric actuator, resonator, etc.). The haptic actuators 840 may be individually or collectively activated in order to communicate information to the user. For example, the haptic actuators 840 may communicate information relating to a graphical user interface displayed on the open display or the immersive display (e.g., warnings, alerts, confirmation of selection of a menu item, etc.). As another example, the haptic actuators 840 may provide tactile feedback relating to configuration of the immersive display (e.g., vibrating to give the feeling of a mechanical detent and/or variable resistance for orienting or positioning the support arm and/or housing), which may, for example, be useful to help guide the user to a more ergonomic setup with the immersive display and/or to guide the user to an optimum relative head-arm/hand configuration for hand-eye coordination while viewing the immersive display (as further described below).

In some variations, multiple haptic actuators 840 may be arranged in a distributed fashion around the housing 820, and may provide directional indications relating to status of other components from the robotic surgical system. For example, a handheld user interface device, which provides the user control over a robotic surgical system, may have a limited workspace within which its movements may be tracked in space and translated into commands for the robotic surgical system. When the handheld user interface device is approaching or has reached a boundary of its trackable workspace, one or more haptic actuators 840 may activate as a directional alert or warning that manipulations of the user interface device may soon be or is now untrackable (e.g., as a left-side boundary of the trackable workspace is approached, a corresponding left-side haptic actuator 840 on the housing may activate). As another example, as a robotic arm is manipulated as the result of the user's actions while engaged with the immersive display, the robotic arm may approach or reach a limit of its physical range of motion. In such instances, one or more haptic actuators 840 may activate as a directional alert or warning to indicate to the user that a current command for motion of the robotic arm is in danger of reaching its physical limits of motion. As another example, during use, the robotic arm may become at risk for colliding with or physically interfering with another object such as another robotic arm, the patient table, a nearby surgical assistant, etc. Similar to the above-described examples, one or more haptic actuators 840 may activate as a directional alert or warning to indicate to the user that the robotic arm is at risk of collision.

Figure 9:
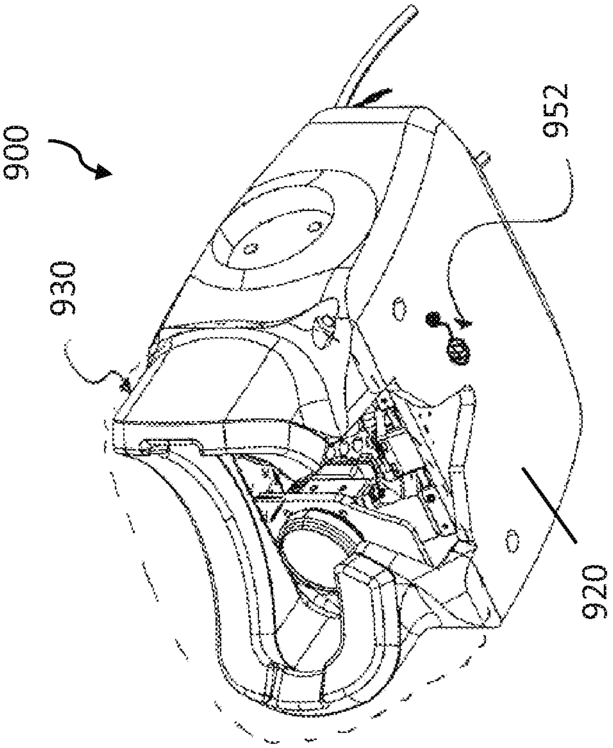
FIG. 9 is a perspective view of an exemplary housing including a microphone in another variation of an immersive display.

In some variations, the housing may include one or more audio devices. For example, as shown in FIG. 9, an immersive display 900 may include housing 920 including at least one microphone 952. The microphone 952 may be located, for example, on a portion of the housing to be positioned near the user's mouth (e.g., an underside of the housing, as shown in FIG. 9), though other locations on the housing may be suitable. In other variations, a separate microphone (e.g., clip-on microphone) may plug into a port located on the housing or support arm. The microphone 952 may be used to communicate with other people such as surgical staff involved in the surgical procedure and/or to enable voice recordings (e.g., communications with surgical staff, dictations for notes such as medical records, etc.). Additionally or alternatively, the microphone 952 may receive vocal commands (e.g., verbal commands or noises such as clicking, blowing, whistling, etc.) for voice control of the robotic surgical system, interactive content of displays, etc. For example, voice control may be used to switch between applications or tasks in the GUI, or control particular features in applications on the GUI such as selecting music, switching views or screens of the GUI, etc. Furthermore, the microphone 952 may be coupled to external voice-controlled devices (e.g., personal cell phone, etc.) to enable hands-free operation of the external voice-controlled device. Some or all of these above-described vocal commands may be accompanied with another user input (e.g., actuation of a foot pedal or other foot-operated controls) operating similar to a clutch. Alternatively, some or all of these vocal commands may be performed without a simultaneous user input clutch.

Figure 10:
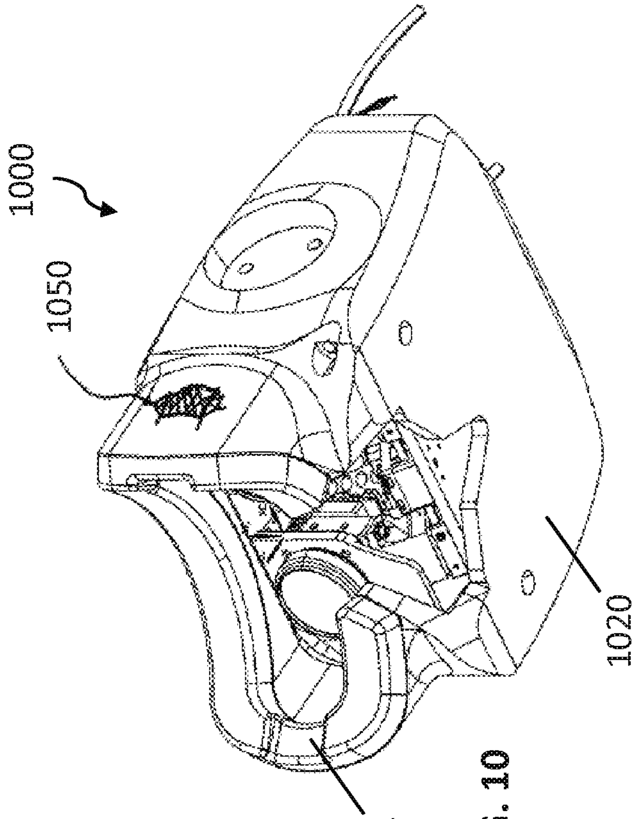
FIG. 10 is a perspective view of an exemplary housing including a speaker in another variation of an immersive display.

As another example, as shown in FIG. 10, an immersive display 1000 may include housing 1020 including at least one speaker 1050. The one or more speakers 1050 may be located, for example, on at least one side of the face frame 1022 and configured to project sound directionally toward the user's ears when the user is engaged with the housing 1020. For example, a speaker 1050 on both left and right sides of the housing may provide stereo sound. However, other locations on the housing may be suitable (e.g., top, bottom). Speakers 1050 may be configured to provide additional information to the user, such as sound accompanying displayed video content, noises and sound effects associated with a graphical user interface (e.g., clicks or tones indicating selection of items in the graphical user interface, alerts or warnings, etc.), and/or sounds augmenting haptic actuator actions for an enhanced, richer experience. The speaker 1050 may also be used to receive communications with other people such as surgical staff (e.g., in conjunction with a microphone 952 described above, the speaker 1050 may facilitate two-way communication) or for phone calls when connected to a phone device. As another example, one or more speakers 1050 may be configured to emit white noise or active noise cancellation for the user. Furthermore, the speaker 1050 may be coupled to one or more external audio devices (e.g., radio, personal music player device, etc.).

In some variations, an immersive display 1100 includes a housing 1120 with one or more auxiliary displays located independent of the 3D display provided by the eyepiece assemblies. Such displays may display, for example, supplemental content (training videos, pre-operative medical images such as CT or MRI scans, etc.) that may be useful for reference during the surgical procedure. In other modes, the displays could additionally or alternatively display primary content (such as endoscopic camera video feed, graphical user interface information, etc.). For example, the housing may include one or more side displays 1140 located adjacent the eyepiece assemblies such that the user may view content on the side displays 1140 in his or her lateral peripheral vision (or with a side glance). As another example, the housing may one or more top displays 1130 located on a top exterior surface of the housing 1120, such that the user may view content on the top display 1140 in his or her upper peripheral vision (or with an upward glance). The auxiliary displays may be actuatable between a viewable position and a hidden or storage position, similar to the shields described above with reference to FIG. 7. For example, the side displays 1140 may be configured to swing laterally inward and outward depending on whether the user wishes to view content on the displays. Similarly, the top display 1130 may be configured to flip up and flip down around a pivoting axis, or slide in and out of a pocket or slot as desired.

Figure 12:
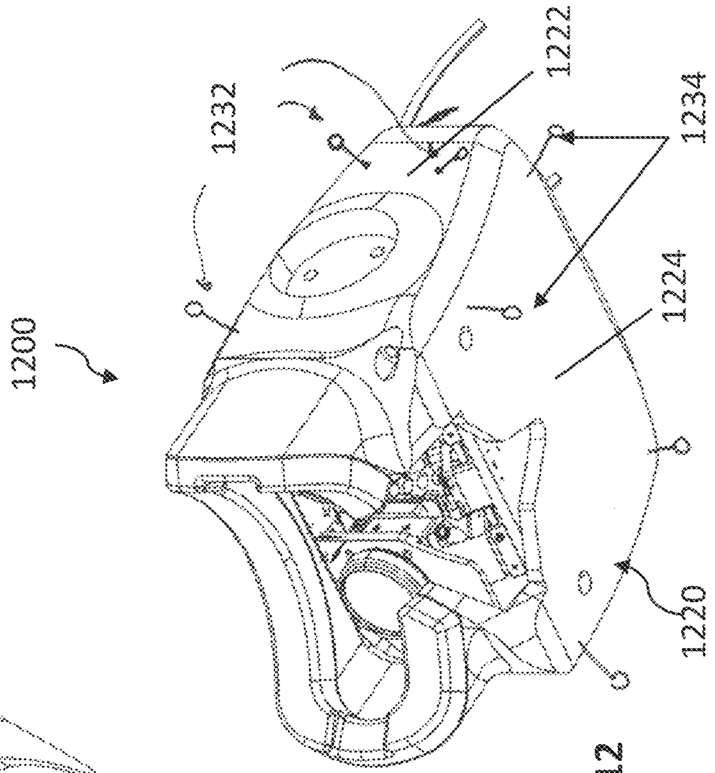
FIG. 12 is a perspective view of an exemplary housing including tracking devices in another variation of an immersive display.

As shown in FIG. 12, in yet other variations, an immersive display 1200 may include a housing 1220 with one or more tracking devices to monitor the position of the housing 1220 in space. The tracking devices may include, for example, electromagnetic transmitters, optical fiducial markers (e.g., optical tracking balls 1232) used in conjunction with overhead or nearby optical sensors, inertial measurement units, etc. Additionally or alternatively, a support arm coupled to housing 1220 may include joint or position encoders on the support arm, potentiometers, etc. for tracking the housing. Tracking the position of the housing 1220 may enable automatic changes in the immersive display content based on position. For example, after detecting with the tracking devices that the housing 1220 has been moved from being engaged with the face of a user to being disengaged and pushed off to a side of the user, the immersive display may transition from a primary display (e.g., endoscopic camera view of the surgical site and surgical tools) to a secondary display (e.g., reference images, etc.). As another example, after detecting with the tracking devices that the housing 1220 is moved to a location inaccessible by the seated user and/or adjacent an open display monitor, the immersive display may transition to a dual-console display in cooperation with the open display or other display unit. As yet another example, after detecting with the tracking devices that the housing 1220 is moved to an extreme location off to the side (e.g., storage position) or is turned around to face away from the user, the immersive display may automatically turn off or revert to an idle or standby state.

The tracking device information may also help enable ergonomic optimization and user alignment with the immersive display for extended use and comfort. For example, the tracking device 1220 may indicate in some circumstances that the housing is slightly not level or is slightly misaligned with the user's eyes and/or hands, and may in response automatically trigger a minor positional adjustment via the support arm to correct the position of the housing relative to the user (e.g., to make the housing level relative to the user's eyes, correct to provide the user with the proper line of sight for viewing the immersive display, etc.).

In some variations, the housing and/or support arm may be configured to keep the housing and eyepiece assemblies generally level and aligned with the user, despite inadvertent minor movements such as vibrations caused by passersby, etc. As such, the housing or other suitable portion of the immersive display may include an accelerometer or other suitable sensor for detecting movements of the housing and/or support arm that are associated with aberrations rather than intentional user interactions. In response to detection of such minor movements, one or more actuators in the support arm may activate as part of an active suspension to compensate for the minor vibrations and keep the display relatively stable and aligned with the user.

Figure 13:
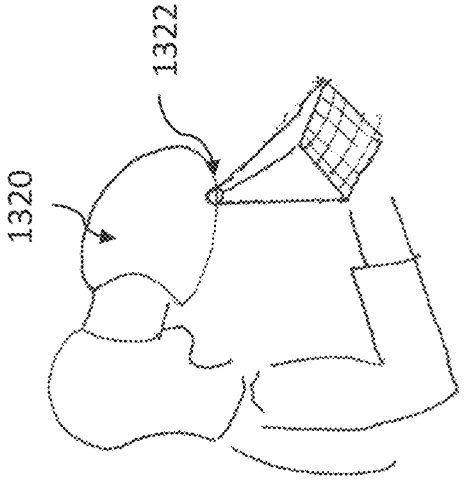
FIG. 13 is a schematic of an immersive display with an outward-facing illuminator for providing outward projections.

In another variation, as shown in FIG. 13, an immersion display may include a housing 1320 having at least one outward-facing illuminator 1322 for projecting one or more reference indicators on a workspace. The illuminator 1322 may include, for example, a laser, LED, other lights, etc. For example, the illuminator 1322 may project a grid, icons, or other references to highlight an optimal position for the user's handheld user interface devices relative to the eyepieces in the immersive display (e.g., to optimally match the endoscopic camera-surgical instrument relationship, as further described below). As another example, the outward illumination may additionally or alternatively be used to improve visibility of specific targets or other components of the system, such as preset locations to dock or set down handheld user interface devices, locations of pedal assemblies or other foot-operated controls, etc. Such improved visibility may involve, for example, illuminated projections of graphical icons or outlines of highlighted or targeted components, and may be useful in situations such as when the user is engaged with the immersive display but able to view the illuminated projections in their peripheral vision (e.g., shields described with respect to FIG. 7 are not obstructing the user's field of view) which assist the user in locating the targeted components.

Eyepieces and Display

As shown in FIG. 2B, at least two eyepiece assemblies, including a left side eyepiece assembly 230L and a right side eyepiece assembly 230R, may be disposed inside the housing 220 and arranged in a binocular fashion. Each eyepiece assembly includes an LCD and/or LED panel display, optics (e.g., lenses, mirrors, etc.), and electronics. For example, in some variations, the eyepiece assemblies may be similar to any suitable eyepiece assemblies that are commercially available for applications including virtual and augmented reality environments (e.g., for military and/or gaming purposes) and are familiar to one of ordinary skill in the art. Collectively, the eyepiece assemblies are configured to provide a 3D display (e.g., stereoscopic) to the user. The 3D display may further be configured to display 2D content. One or more actuators may be integrated in or coupled to at least one eyepiece assembly, such as for adjusting the relative positions between the eyepiece assemblies (e.g., for adjustment of interpupillary distance) and/or depth within the housing (e.g., for adjustment of distance to the user's eyes), etc. Other electronics associated with the eyepiece assemblies and other components in the housing may relate to controlling and managing image signals to the display and power supply to the various components. In some variations, the electronics may include one or more wireless batteries or other power sources for supplying power to the electrical components of the immersive display, though additionally or alternatively, immersive display may be coupled to a wired primary or backup power supply.

In some variations, a series of multiple lenses may additionally or alternatively be included in the housing and configured to provide a curved or panoramic image that continuous spans a wide visual frame. Alternatively, the series of multiple lenses may also be configured into two or more divided, split screens showing discrete content across the available visual frame. Furthermore, lenses or other corrective mechanisms may be selectively provided in conjunction with the eyepiece assemblies to provide vision correction (e.g., for near-sightedness, far-sightedness, astigmatism, etc.).

Figure 11:
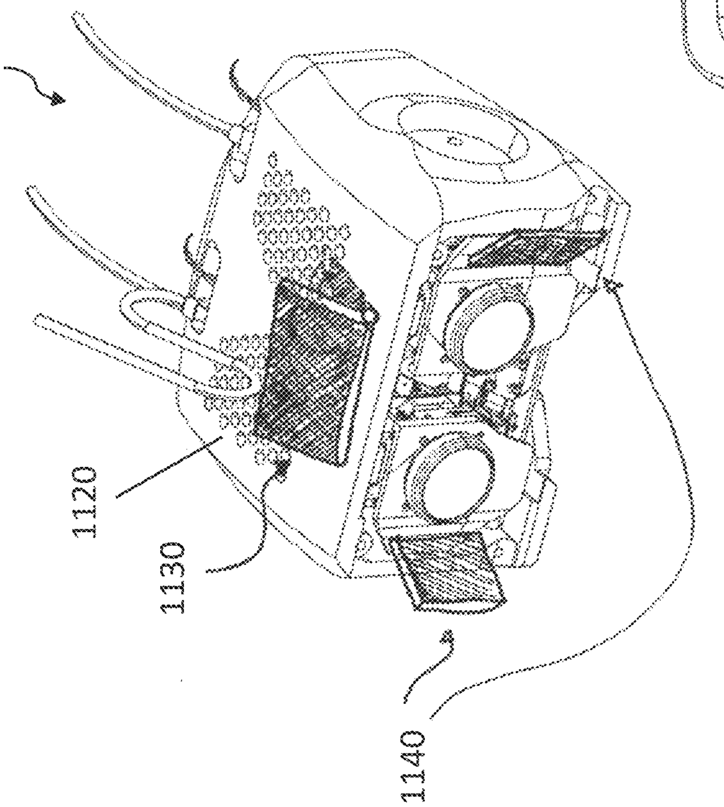
FIG. 11 is a perspective view of an exemplary housing including auxiliary displays in another variation of an immersive display.
Figure 17:
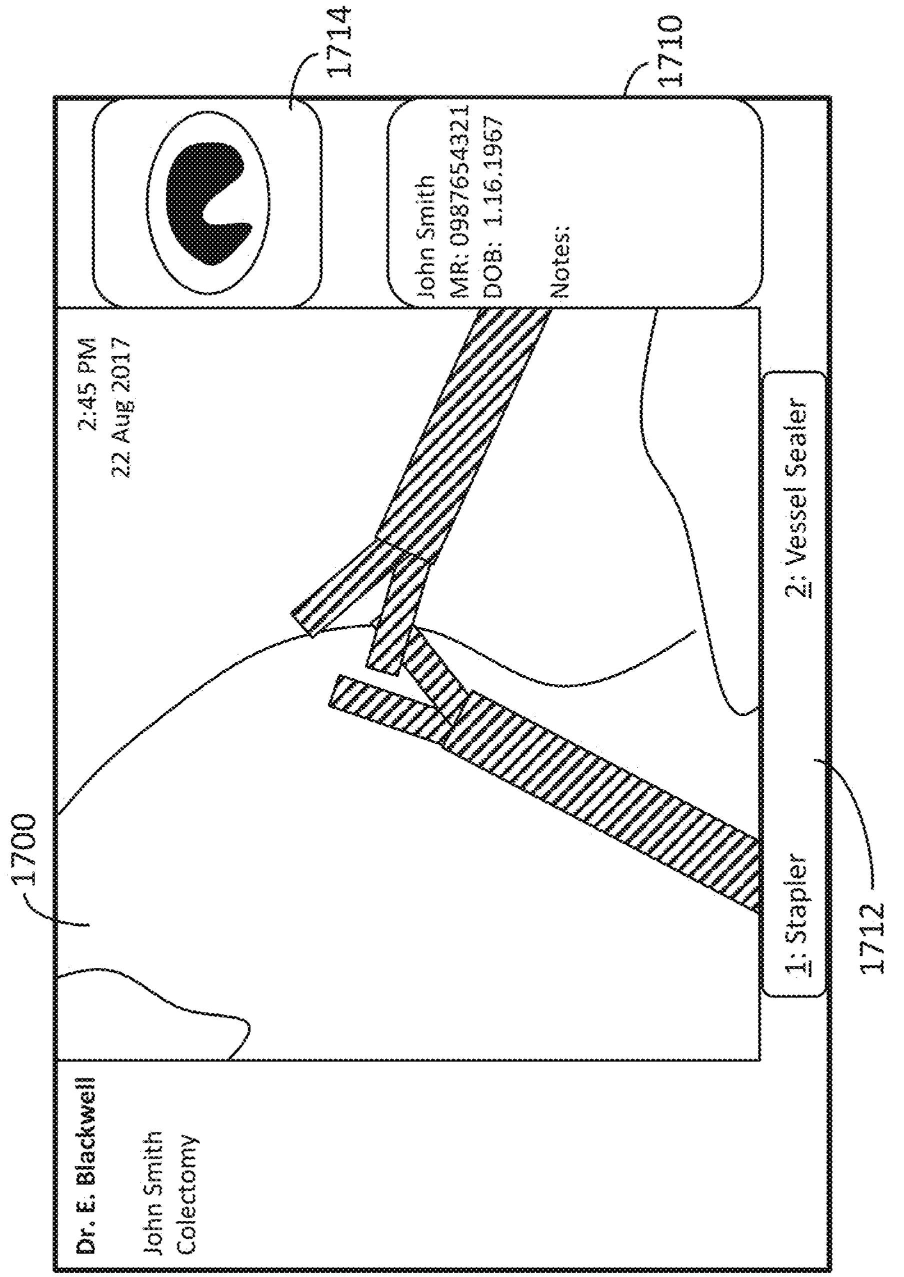
FIG. 17 depicts an exemplary displayed image and graphical user interface shown in an immersive display.

Generally, the eyepiece assemblies may be configured to display a range of information to the user when the user is engaged with the immersive display, including but not limited to 3D information, video, static images, GUIs, interactive controls, etc. The eyepiece assemblies 230 may serve as a supplemental display to other displays relating to the robotic surgical system such as an open display (e.g., display 128 as shown in FIG. 1B), auxiliary displays on the immersive display (e.g., side and/or top displays 1140 and 1130 as shown in FIG. 11), and any other auxiliary displays (e.g., open displays coupled to a seat in a user console, etc.). As such, one or more of these displays may be designated a primary display intended for principal viewing. An example of a primary display is a GUI such as that shown in FIG. 17. For example, a GUI may display endoscopic image data 1700 (e.g., from an endoscopic camera placed inside the patient), and/or patient data 1710 (e.g., name, medical record number, date of birth, various suitable notes, etc.). The primary display may further include a control panel 1712 and one or more medical images 1714 (e.g., pre-operative images of patient tissue). The control panel 1712 may include information such as a left tool number, a left tool name, a left tool function, and the like. Similar information can be supplied for a right tool arm. However, other suitable GUIs or other display content may appear on a primary display. Furthermore, one or more of the displays may be designated a secondary display for providing supplemental content (e.g., reference images or videos). Various user interactions may cause the displays to change their designations as a primary display, secondary display (or other suitable classification of display), and thus their displayed content type, as further described below.

The housing may include eye-tracking sensors or cameras (e.g., disposed in or near the eyepiece assemblies 230 shown in FIGS. 2A and 2B), which may be used to detect the user's gaze, which may be used for a safety lock-out or interlock feature for restricting operation of the robotic surgical system (e.g., with iris code detection, as further described below), for changing controls in the system, modifying the immersive display content, for being interpreted as user input for navigation of a GUI on one of the displays, as another suitable metric for evaluating the use of the immersive display and/or robotic surgical system, etc. Additionally or alternatively, eye tracking or pupil sensing may be used to automatically adjust the interpupillary distance (IPD) between the two eyepieces based on a detected distance between the user's pupils, as further described below. Eye-tracking may also be used, in some variations, to monitor the fatigue level of the user, such as during extended use of the robotic surgery system.

It should be understood that although some specific examples of sensor types, sensor locations, and sensor functions in the immersive display have been discussed above, a wide variety of other sensors and sensor types may additionally or alternatively be located throughout the various components of the immersive display (e.g., support arm, housing) in order to capture information about the user and/or for receiving user input as interactive user controls. For example, the immersive display system may include various sensors and other components for use as further described below.

Controller

The immersive display may include a control system that governs behavior of the immersive display. For example, the control system may include one or more controllers 1900 in the including one or more processors (e.g., microprocessor, microcontroller, application-specific integrated circuit, field programmable gate array, and/or other logic circuitry). Controller 1900 may be in communication with one or more other components of a user console 1940 (e.g., handheld user interface devices, foot-operated user interface devices, open display, etc.). The controller 1900 may further be in communication with a storage device 1930 for storing various items in memory such as biometrics of a user, user preferences, user profiles, etc. The controller 1900 may further be in communication with subcontrol modules such as a support arm controller 1910 configured to control components of the support arm including but not limited to various motors 1912 for actuating the support arm, and various sensors 1914, and any other components of the support arm such as those described herein. Furthermore, the controller 1900 may be communication with a housing controller 1920 configured to control components of the housing of the immersive display, including but not limited to eyepiece assemblies 1922, sensors 1924, motors 1926, and any other components within the display housing such as those described herein. Alternatively, the controller 1900 may interface directly with components of the support arm and/or housing, thereby omitting subcontrol modules 1910 and 1920 for the support arm and the housing, respectively.

Operation of an Immersive Display

Generally, the immersive display may be operated in one or more of several modes or states. The transitions between these modes and/or any other modes may be directed by the user via interactions with sensors of the immersive display (e.g., in the support arm and/or housing), and additionally or alternatively with other supplemental sensors in a user console with which the immersive display is associated. As such, the switching between various modes may, for example, be handled by a state machine/controller.

In a setup mode, the immersive display is initialized for the user when the user interacts with the immersive display system. This mode may be suitable, for example, during preparation for or at the beginning of a surgical procedure performed with an associated robotic surgical system. This mode may also be suitable whenever the user engages with the immersive display, for the first time for a particular surgical procedure and/or, in some variations, at selected interim times thereafter (e.g., after a period of disuse of the immersive display).

In some variations, a setup mode may be characterized by a safety lock-out or interlock feature implemented in the immersive display, such that one or more sensors may enable operation of robotic surgical system. In one variation, one or more sensors may be configured to identify the user for authorization to operate the robotic surgical system. For example, such a sensor may be incorporated in a camera configured to detect an iris code of a user, where the controller compares the detected iris code to stored iris codes in a database associated with authorized users and enables operation of the robotic surgical system if the detected iris code corresponds to that associated with an authorized user. Other sensors suitable for detecting a unique biometric parameter may additionally or alternatively be included for identifying the user, such as an IR sensor for detecting a heat signature, electronics for performing voice recognition, etc. If there is no indication that the user is an authorized user of the robotic surgical system, the immersive display and/or other components of a user console may remain powered off, idle, or otherwise nonresponsive if the user attempts to operate the robotic surgical system. Furthermore, upon identifying the user via iris code detection and recognition, the controller may load user-associated presets and/or preferences, such as seat position adjustment settings for a seat assembly in the user console, favorite GUI representations, etc.

In another variation, one or more sensors may be configured to determine proper alignment or positioning of the face of the user with the housing, eyepiece assemblies, or other suitable part of the immersive display. For example, such a sensor may be an optical sensor configured to perform eye-tracking, where the controller analyzes the user's gaze to determine whether the user's eye is in an optimum location relative to the eye assemblies. If proper positioning (e.g., distance from eye assemblies and/or lateral alignment) is determined, then the controller may enable operation of the robotic surgical system. If there is no indication that the user's eyes are properly positioned, the immersive display and/or other components of a user console may remain powered off, idle, or otherwise nonresponsive if the user attempts to operate the robotic surgical system. Additionally or alternatively, if there is improper positioning, then the immersive display may automatically adjust (e.g., actuate the support arm to move the housing an incremental amount to compensate for the misalignment) and/or provide an indication to the user to adjust his or her position relative to the immersive display. Other sensors may additionally or alternatively be included on or in the housing, such as pressure, distance, or temperature sensors, etc. (e.g., on a user-interfacing side of the face frame) that provide an indication of the user's presence and/or position relative to the immersive display. These other types of sensors may, for example, be additionally utilized to provide redundancy with the eye-tracking sensors for safety purposes.

In some variations, a setup mode may be characterized by an adjustment of interpupillary distance (IPD) between the two eyepiece assemblies to accommodate anthropometric ranges among different users. The controller may perform such adjustment automatically, such as by using eye-tracking to determine the user's IPD and actuating the eyepiece assemblies closer or farther apart until the IPD between the eyepiece assemblies are approximately matching. Additionally or alternatively, the IPD adjustment may be manual, such as with a geared arrangement controlled by a knob or electronic switch. In one variation, the IPD distance for a particular user may be stored in memory and associated with a user profile in a database as part of the user's settings and preferences, such that at a subsequent time when the user is identified or logs in as a user of the immersive display, the controller may retrieve the user's profile and automatically adjust the IPD between the eyepieces to match the user's IPD. Some or all of these user settings and preferences may additionally or alternatively be determined based on iris code recognition applied to the user.

In yet other variations, a setup mode may be characterized by an adjustment of other immersive display settings in accordance with the user's settings and preferences stored in the user's profile. For example, after identifying the user and retrieving the user's profile from a database of stored user profiles, the controller may adjust the support arm to a preferred configuration (e.g., left-side or right-side support arm configuration relative to the user, position of the support arm and housing, etc.).

After the immersive display is set up for a user, the immersive display presents information to the user relating to the robotic surgical system. Additionally, at least one sensor (e.g., eye-tracking sensors to follow the user's gaze and/or pressure sensors or other sensors included in the housing, etc.) may be configured to detect a head gesture of the user, and the controller may interpret head gestures of the user and respond to the interpreted head gestures according to the interpretation of the head gestures of the user. Other sensors such as eye-tracking may indicate other user intent.

In some variations, in response to a detected head gesture of the user, the support arm may be configured to move the housing to track the head gesture such that when the user repositions himself or herself while engaged with the housing of the immersive display, the support arm actuates the housing to move in a corresponding manner to maintain the engagement. For example, if the user leans back in his or her seat, or turns his or her head to the left or right, then the support arm may actuate the housing to follow the user's head as if the housing were coupled directly to the user's head with straps or the like. This tracking of head gestures enables the user to adjust his or her posture without having to disengage from the immersive display, so the user may be able to adjust his or her posture more frequently, thereby improving ergonomic qualities of the system. The controller may distinguish between a head movement relating to postural adjustment from a head gesture relating to intentional disengagement based on parameters such as amount and/or velocity of motion (e.g., a relatively significant and quick head gesture may be interpreted as intentional disengagement from the immersive display). When the controller determines that the user does wish to disengage from the immersive display (e.g., to view the open display, to take a break, etc.), the support arm may abstain from tracking the head gesture and allow the user to separate from the immersive display.

The immersive display may also use any of the above-described sensors (e.g., pressure sensors, distance sensors, contact sensor, switch sensors, eye-tracking sensors, etc.) to monitor head gestures intended for changing controls in the systems, modifying the display, adjusting the housing or support arm configuration, other operation of the robotic surgical system, etc. For example, a user's quick nod upwards might result in selection of a "virtual window" mode that changes the view displayed in the immersive display to the video feed from outward-facing cameras. As another example, a user's slight head turn to the left or right and/or prolonged gaze at a displayed icon may enable navigation (swiping through GUI screens, selection of icons, etc.) through a GUI displayed on the immersive display or other display. As yet another example, another combination of one or more user interactions sensed by the immersive display (head gestures, eye tracking, etc.) may enable toggling between control of different robotic arms, such as between an robotic arm used for manipulating an endoscopic camera and another robotic arm used for manipulating a surgical tool in a "camera clutch" mode. As yet another example, another combination of one or more user interactions sensed by the immersive display may be used to toggle between using the immersive display as a primary display and using the open display (e.g., display 128 shown in FIG. 1B) as a primary display.

In some variations, a user's intentional directional head gestures (optionally in combination with another simultaneous input to another sensor or control operating as a clutch, such as depressing a foot pedal, or holding onto a handle with sensors) might result in modifying the endoscopic camera view that is displayed. For example, while simultaneously activating a clutch, the user may lean in to command a camera view zoom in, lean out to command a camera view zoom out, turn his head left or right to command a camera view pan left or right, or tilt his head forward or backward to command a camera view tilt forward or backward. In this manner, a user may, while holding two handheld user interface devices, may simultaneously operate at least three instruments (e.g., two instruments controlled by two handheld user interface devices held by two hands of the user and a camera instrument controlled with the user's head gestures).

However, the controller may interpret inputs from various combinations of sensors in any suitable manner for determining user intent. Furthermore, the manner in which various combinations of head gestures and/or other sensed user interactions are mapped to specific control commands may be customized for different users and stored as user preference in a user's profile, to be loaded during setup of the immersive display.

Figure 14:
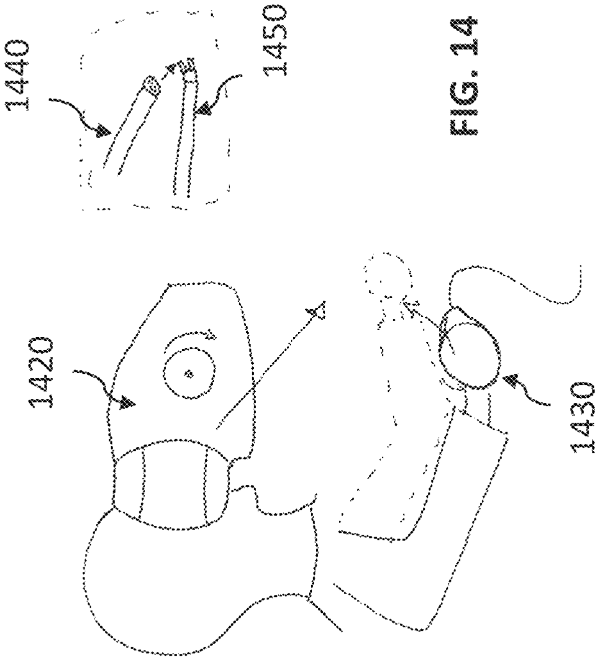
FIG. 14 is a schematic of an exemplary immersive display setup exhibiting correspondence between a relative spatial relationship of the eyepiece assemblies and user hand positions and a relative spatial relationship of the endoscopic camera and a surgical instrument.

Furthermore, in some variations as shown in FIG. 14, the immersive display may be configured to provide guidance for maintaining a correspondence between a relative spatial relationship of the housing 1420 and user hand position 1430 and a relative spatial relationship of the endoscope camera 1440 and a surgical instrument 1450. When the user is engaged with the immersive display, the user may be simultaneously viewing (through a displayed endoscopic camera video feed) the surgical site and holding handheld user interface devices for remotely controlled surgical instruments at the surgical site. For the user to maintain sufficiently accurate proprioception (e.g., substantially accurate spatial mapping between the user's immersive environment and the real surgical site environment), the relative position of the user's head and the user's hands is preferably substantially similar to the relative position of the endoscopic camera and the remotely controlled surgical instruments. To provide guidance for maintaining this correspondence, the immersive display may, for example, display to the user graphical representations or icons for where the user should position his or her hands for the current housing location and orientation. Such graphical representations may be overlaid on a current displayed image, or may be displayed separately (e.g., in a calibration mode). Additionally or alternatively, the immersive display may provide audio cues or haptic cues to notify when the user's head and hands are in the proper relationship (e.g., audio tones to suggest readjustment of the user's hands). In some variations, the controller may implement corrective adjustments (e.g., adjust position of the immersive display) to help maintain suitable correspondence between the relative spatial relationship of the housing 1420 and user hand position 1430 and the relative spatial relationship of the endoscope camera 1440 and a surgical instrument 1450. Furthermore, other motion coupling, biasing, and/or feedback algorithms relating the position of one or more immersive display components (housing, support arm, etc.) to other robotic surgical system components (e.g., handheld user interface devices, foot-operated controls, etc.) may be included. Such algorithms may, for example, apply optimum hand-eye coordination factors in mathematical transformations to map the relationships between the various components.

Figure 18B:
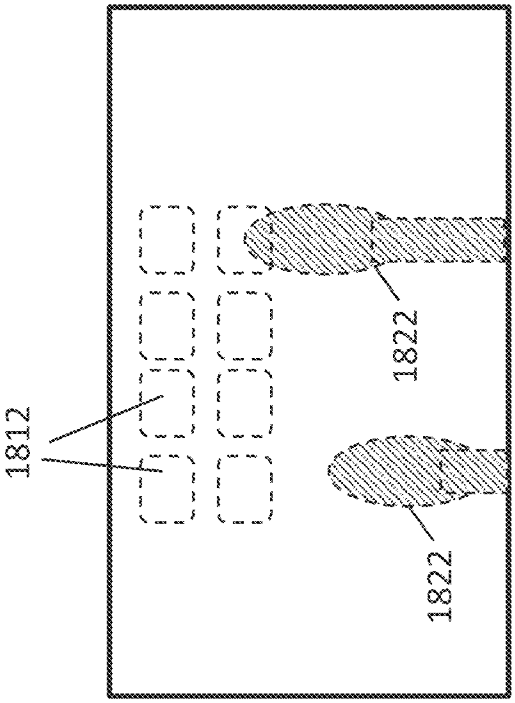
FIG. 18B is an exemplary display in an immersive display showing a visual representation of foot positions relative to target foot positions.
Figure 18A:
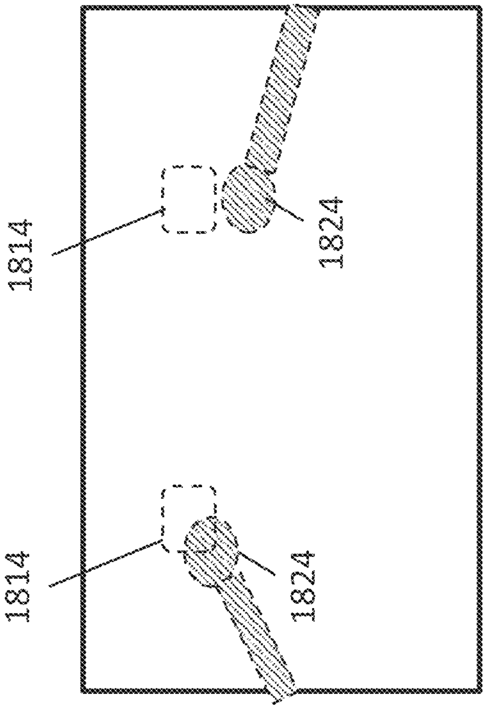
FIG. 18A is an exemplary display in an immersive display showing a visual representation of user hand positions relative to target hand positions.
Figure 19:
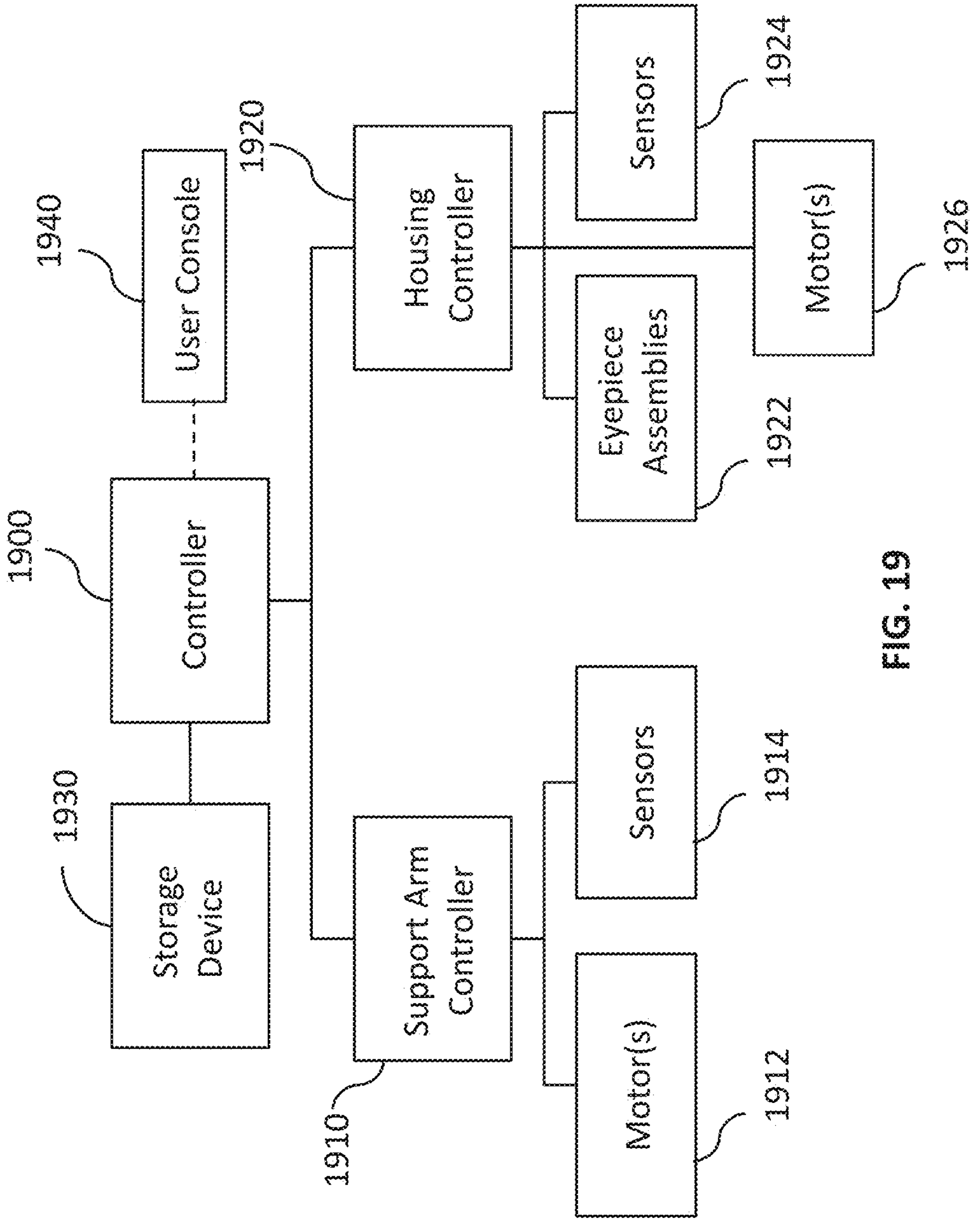
FIG. 19 is an exemplary schematic of a control system for controlling various components in and associated with one variation of an immersive display.

In some variations, the immersive display may be configured to provide one or more visual cues to the user for repositioning at least one of a user hand position and a user foot position relative to target locations (e.g., locations of handheld or foot-operated user interface devices). Audio and/or haptic actuator cues (e.g., beeps or vibrations in the face frame for indicating confirmed positional placement) from the immersive display may additionally or alternatively provide for such purposes. For example, as shown in FIG. 18A, the immersive display may show visual representations of one or more hand positions (e.g., silhouettes 1824) relative to one or more graphical representations 1814 (e.g., bubbles or outlines) of a target hand location, such the location of a dock or resting place for handheld user interface devices. As another example, as shown in FIG. 18B, the immersive display may show visual representations of one or more foot positions (e.g., silhouettes 1822) relative to one or more graphical representations 1814 (e.g., bubbles or outlines) of a target foot location, such as the location of a foot pedal. The visual representations of the user's hand and/or foot positions may be derived, for example, from source data obtained 3D cameras or sensors, IR projections, LIDAR, etc. aimed in the user workspace in which the user's hands and feet are present. These visual and graphical representations may be overlaid with an existing, primary displayed image (e.g., camera view). Similar visual and graphical representations may also be used to provide a visual reminder to the user to dock handheld user interface devices at a particular designated location (e.g., on a component of a user console, or on a designated hook or docking location on the support arm and/or housing of the immersive display).

The one or more sensors may additionally or alternatively be configured to detect the competency of a user in the seat assembly, such as to check that the user operating the surgical instrument is sufficiently well-rested and/or sober. For example, an optical sensor for performing eye tracking may be used to predict whether a user is sleep-deprived or fatigued (e.g., based on eye movement, blink rate, etc.). Furthermore, a chemical sensor (e.g., breathalyzer) may be included to check for sobriety based on ethanol traces and the like. These kinds of events may, for example, trigger at least an audible/visible alarm or other warning, and/or a disablement of the controls in order to protect the patient undergoing a surgical procedure.

In some variations, the immersive display may be operable in a gross positioning mode and/or a fine positioning mode when being positioned. In a gross positioning mode, the support arm and/or the housing may be movable in a relatively high number of degrees of freedom (e.g., no restrictions such that all support arm joints move freely, or few restrictions on motion, such as only prevention of tilt). In contrast, in a fine positioning mode, the support arm and/or the housing may be movable in a relatively low number of degrees of freedom less than that in the gross positioning mode. For example, fine positioning may enable only a portion of the support arm joints to move freely (e.g., for tilt and/or height adjustments).

It should be understood that although the immersive display is described herein with particular reference to controlling a robotic surgical system, features of the immersive display (e.g., ergonomic repositioning) are relevant to other applications. For example, the support arm may be used in conjunction with a virtual reality headset such as for gaming and/or engineering development on a virtual reality environment. Additionally, to help reduce user fatigue with other head-mounted displays such as for military purposes, the support arm described herein may be used to help off-load and support weight of the head-mounted display through gravity balancing or similar weight compensation, while maintaining a "floating" configuration and permitting the head-mounted display to be moved freely. Even further, the immersive display housing as described herein may be detachable (or the support arm omitted) in order to use the housing as a head-mounted display.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

The invention claimed is:

1. A robotic surgical system comprising:
- an immersive display that comprises:
  - a support arm,
  - a housing mounted to the support arm and configured to provide a three-dimensional (3D) display of at least one image, and
  - at least one sensor;
- at least one processor; and
- memory having instructions which when executed by the at least one processor causes the robotic surgical system to maintain, based on the at least one sensor detecting an intentional head gesture of a user of the robotic surgical system, a relative spatial relationship of the housing and a hand of the user by providing visual cues to position the hand of the user at a target location in space.

2. The robotic surgical system of claim 1, wherein the housing comprises one or more haptic actuators that are configured to provide tactile feedback to the user.

3. The robotic surgical system of claim 2, wherein the one or more haptic actuators are arranged in a distributed configuration around the housing, wherein the tactile feedback of at least one of the haptic actuators provides a directional indication relating to a status of a component of the robotic surgical system arranged around the immersive display.

4. The robotic surgical system of claim 3, wherein the at least one of the haptic actuators that provide the directional indication are on a side of the housing that is closest to the component of the robotic surgical system with respect to a remainder of the one or more haptic actuators.

5. The robotic surgical system of claim 1, wherein the housing comprises one or more tracking devices configured to monitor a position of the housing in space.

6. The robotic surgical system of claim 5, wherein the memory comprises further instructions to:
- receive the at least one image captured by a surgical instrument of the robotic surgical system; and
- provide, responsive to a determination that the position of the housing has changed, a 3D display of one or more different images than the at least one image captured by the surgical instrument.

7. The robotic surgical system of claim 5 further comprises a seat to which the support arm of the immersive display is coupled, wherein the memory comprises further instructions to turn off the immersive display or set the immersive display to a standby state in response to a determination that the position of the housing in space is inaccessible to the user while seated in the seat.

8. The robotic surgical system of claim 1, wherein the visual cues are provided by at least one of:

causing an outward-facing illuminator to produce illuminated projections to highlight the target location in space, or displaying, on the immersive display, a graphical representation of the target location in space.

9. The robotic surgical system of claim 1, wherein the memory has further instructions to move the support arm to maintain engagement between the housing and a face of the user based on the detected intentional head gesture, wherein the relative spatial relationship is maintained responsive to the movement of the support arm.

10. A method for operating a robotic surgical system that includes a three-dimensional (3D) display, the method comprising:

detecting, using at least one sensor, a head gesture of a user;

displaying at least one image on the 3D display that is disposed in a housing; and maintaining, based on the detecting of the head gesture of the user, a relative spatial relationship of the housing and a hand of the user by providing visual cues to position the hand of the user at a target location in space.

11. The method of claim 10, wherein the housing comprises one or more haptic actuators that are arranged in a distributed configuration around the housing, wherein at least one of the haptic actuators provides a directional indication relating to a status of a component of the robotic surgical system arranged around the housing.

12. The method of claim 11, wherein the at least one of the haptic actuators that provide the directional indication are on a side of the housing that is closest to the component of the robotic surgical system with respect to a remainder of the one or more haptic actuators.

13. The method of claim 10, wherein the housing comprises one or more tracking devices configured to monitor a position of the housing in space.

14. The method of claim 13 further comprising:

receiving the at least one image captured by a surgical instrument of the robotic surgical system; and providing, responsive to a determination that the position of the housing has changed, a 3D display of one or more different images than the at least one image captured by the surgical instrument.

15. The method of claim 13, wherein the robotic surgical system comprises a seat to which the 3D display is coupled, wherein the method further comprises turning off the 3D display or setting the 3D display to a standby state in response to a determination that the position of the housing in space is inaccessible to the user while seated in the seat.

16. The method of claim 10, wherein the visual cues are provided by at least one of:

causing an outward-facing illuminator to produce illuminated projections to highlight the target location in space, or displaying, on the 3D display, a graphical representation of the target location in space.

17. The method of claim 10 further comprising moving the housing to maintain engagement between the housing and a face of the user based on the head gesture, wherein the relative spatial relationship is maintained responsive to the movement of the housing.

18. An immersive display for use in a robotic surgical system, comprising:

a housing mounted to a support arm and configured to provide a three-dimensional (3D) display of at least one image; and at least one sensor, wherein the immersive display is configured to maintain, based on the at least one sensor detecting an intentional head gesture of a user of the robotic surgical system, a relative spatial relationship of the housing and a hand of the user by providing visual cues to position the hand of the user at a target location in space.

19. The immersive display of claim 18, wherein the housing comprises one or more haptic actuators that are arranged in a distributed configuration around the housing, wherein at least one of the haptic actuators provides a directional indication relating to a status of a component of the robotic surgical system arranged around the immersive display.

20. The immersive display of claim 18, wherein the housing comprises one or more tracking devices configured to monitor a position of the housing in space, wherein the immersive display is further configured to:

receive the at least one image captured by a surgical instrument of the robotic surgical system; and provide, responsive to a determination that the position of the housing has changed, a 3D display of one or more different images than the at least one image captured by the surgical instrument.

* * * * *